United States Patent
Ho et al.

(10) Patent No.: US 9,084,863 B2
(45) Date of Patent: Jul. 21, 2015

(54) RESPIRATORY PATIENT INTERFACES

(75) Inventors: Peter Chi Fai Ho, Pittsburgh, PA (US);
Jerome Matula, Jr., Apollo, PA (US);
Liz Margaria, Pittsburgh, PA (US);
Richard A. Sofranko, Finleyville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 416 days.

(21) Appl. No.: 13/060,113

(22) PCT Filed: Aug. 15, 2009

(86) PCT No.: PCT/IB2009/053603
§ 371 (c)(1),
(2), (4) Date: Feb. 25, 2011

(87) PCT Pub. No.: WO2010/023590
PCT Pub. Date: Mar. 4, 2010

(65) Prior Publication Data
US 2011/0155140 A1  Jun. 30, 2011

Related U.S. Application Data

(60) Provisional application No. 61/091,551, filed on Aug. 25, 2008.

(51) Int. Cl.
*A61M 16/06* (2006.01)
*A61B 7/00* (2006.01)
*A61M 16/04* (2006.01)
*A61M 16/08* (2006.01)

(52) U.S. Cl.
CPC ......... *A61M 16/0666* (2013.01); *A61M 16/049* (2014.02); *A61M 16/0488* (2013.01); *A61M 16/0683* (2013.01); *A61M 16/0694* (2014.02); *A61M 16/08* (2013.01); *A61M 16/0816* (2013.01); *A61M 16/0875* (2013.01); *A61M 2205/6045* (2013.01)

(58) Field of Classification Search
USPC ............ 128/205.11, 206.11, 206.12, 206.21, 128/206.24, 206.27, 206.28, 207.11, 207, 128/12, 207.18, 205.25, 206.26, 206.15, 128/207.13, 207.12
See application file for complete search history.

(56) References Cited

U.S. PATENT DOCUMENTS

| | | | | |
|---|---|---|---|---|
| 4,915,105 A * | 4/1990 | Lee | ........................... | 128/205.27 |
| 7,370,652 B2 * | 5/2008 | Matula et al. | ............ | 128/206.11 |
| 7,942,150 B2 * | 5/2011 | Guney et al. | ............. | 128/207.18 |
| 7,943,150 B2 * | 5/2011 | Emery et al. | ................ | 424/234.1 |

(Continued)

FOREIGN PATENT DOCUMENTS

| WO | WO2004073778 A1 | 9/2004 | |
|---|---|---|---|
| WO | WO 2006074516 A1 * | 7/2006 | ............ A61M 16/06 |

(Continued)

*Primary Examiner* — Tan-Uyen (Jackie) T Ho
*Assistant Examiner* — Mark Wardas
(74) *Attorney, Agent, or Firm* — Michael W. Haas

(57) ABSTRACT

Various embodiments of respiratory patient interfaces that may be used to treat a variety of disorders involving upper airway obstruction, such as, without limitation, Obstructive sleep apnea (OSA), obstructive sleep hypopnea, and upper airway resistance syndrome (UARS). A number of the embodiments employ a nasal pillow assembly including a frame that supports a nasal pillow sleeve and a clip that is slid over a flange of the fame to couple the nasal pillow sleeve to the frame.

2 Claims, 22 Drawing Sheets

(56) References Cited

U.S. PATENT DOCUMENTS

2005/0205096 A1\* 9/2005 Matula et al. ............ 128/207.11
2009/0151729 A1\* 6/2009 Judson et al. ............ 128/207.13

FOREIGN PATENT DOCUMENTS

WO WO2007048174 A1 5/2007
WO WO2007053878 A1 5/2007

\* cited by examiner

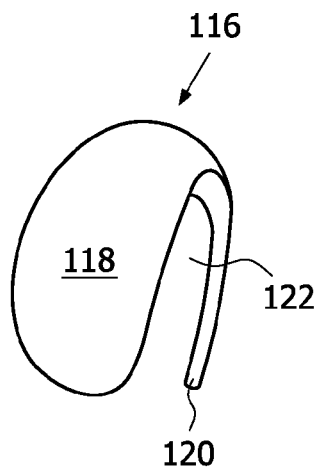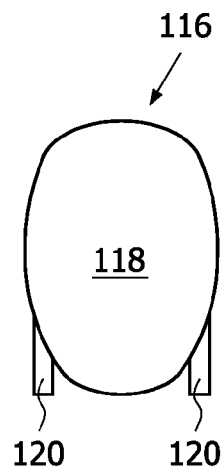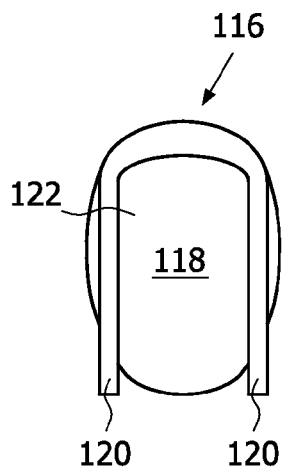
FIG. 16  FIG. 17  FIG. 18
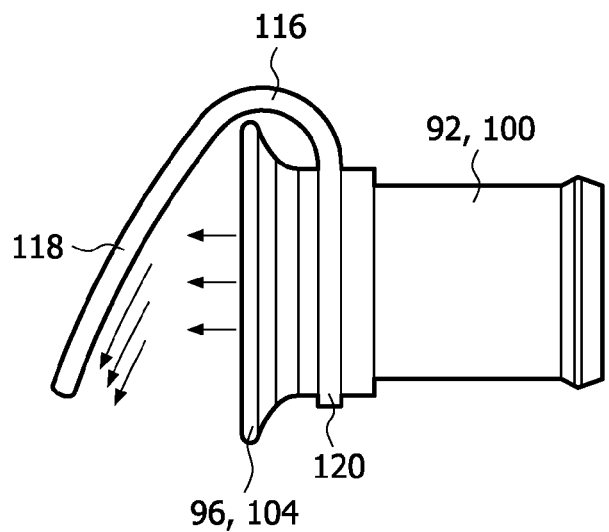
FIG. 19

RESPIRATORY PATIENT INTERFACES

This patent application claims the priority benefit under 35 U.S.C. §119(e) of U.S. Provisional Application No. 61/091,551 filed on Aug. 25, 2008, the contents of which are herein incorporated by reference.

The present invention relates to respiratory patient interfaces used to deliver a gas to a user, and in particular to various embodiments of respiratory patient interfaces that may be used to treat a variety of disorders involving upper airway obstruction.

Obstructive sleep apnea (OSA), obstructive sleep hypopnea, and upper airway resistance syndrome (UARS) are among a variety of known disorders characterized by episodes of complete or partial upper airway obstruction during a state of diminished consciousness, such as sleep, anesthetization, or post anesthesia. OSA, hypopnea, and UARS cause intermittent interruption of ventilation during sleep with the consequence of potentially severe oxyhemoglobin desaturation. Typically, those afflicted with OSA, hypopnea, and UARS experience repeated, frequent arousal from sleep in response to the oxygen deprivation. The arousals result in sleep fragmentation and poor sleep continuity.

Consequences of OSA, hypopnea, and UARS may include debilitating daytime sleepiness and cognitive dysfunction, systemic hypertension, cardiac dysrythmias, pulmonary arterial hypertension and congestive heart failure. Other consequences may include a predisposition to myocardial infarction, angina pectoris, stroke, right ventricular dysfunction with cor pulmonale, carbon dioxide retention during wakefulness as well as during sleep, and continuous, reduced arterial oxygen tension. Moreover, the cognitive impairment resulting from OSA, hypopnea, and UARS puts those afflicted at elevated risk of accidents.

The pathogenesis of the airway obstruction that characterizes OSA, hypopnea, and UARS can include both anatomic and functional abnormalities of the upper airway that result in increased airflow resistance. Such abnormalities may include narrowing of the upper airway due to suction forces created during inspiration, the effect of gravity pulling the tongue back to appose the pharyngeal wall, and insufficient muscle tone in the upper airway dilator muscles, among others. It is also believed that excessive soft tissue in the anterior and lateral neck, as commonly observed in obese persons, can apply sufficient pressure to internal structures to narrow the upper airway and restrict air flow.

Conventional treatment of OSA, hypopnea, and UARS has included surgical intervention, such as uvalopalotopharyngoplasty, gastric surgery for obesity, mandibular advancement procedures, maxillo-facial reconstruction, and tracheostomy. However, surgery potentially involves considerable risk of post-operative morbidity and mortality. In addition, the failure rate of surgery is disturbingly high. Pharmacological therapy has also been proposed to treat OSA, hypopnea, and UARS; however, results have been generally disappointing.

More recently, various positive airway pressure therapies applied during sleep have been used to treat OSA, hypopnea, and UARS patients. During such treatment, positive pressure is applied in the upper airway to splint or support the airway open, thereby preventing its collapse and the resultant airway obstruction. A typical positive airway pressure device comprises a flow generator (e.g., a blower) that delivers gas via a delivery conduit to a patient interface, such as a mask or nasal pillow. It is also known to deliver the positive airway pressure therapy as a continuous positive airway pressure (CPAP), a variable airway pressure, such as a bi-level pressure that varies with the patient's respiratory cycle (Bi-PAP), or an auto-titrating pressure that varies with the monitored condition of the patient. Pressure support therapies are also provided to treat other medical and respiratory disorders, such as Cheynes-Stokes respiration, congestive heart failure, and stroke.

Many patient interfaces are known in the art. These interfaces include nasal pillows with prongs which fit into the nares of the patient, nasal masks which fit over the patient's nose, nasal-oral masks that fit over the mouth and nose, and full face masks which fit over the patient's entire face. It is known to maintain such interfaces on the face of a patient by a headgear that wraps around the head of the patient. A typical headgear includes flexible, adjustable straps that extend from the nasal pillow and/or mask to attach it to the patient.

For such devices to be effective, two competing goals need to be balanced: comfort and support. If the interface proves to be uncomfortable, patient compliance will be low. Comfort may be enhanced by reducing the area of contact between the interface and the patient and/or by using of a soft, lightweight, flexible material. In contrast, to enhance the ability of the interface to support its weight and associated hoses and attachments, the interface should ideally be constructed from a rigid material and have a large contact area between the interface and the patient.

FIGS. 1 and 2 are isometric and exploded/disassembled views, respectively, of one prior art patient interface device 2 which attempts to balance the competing goals of comfort and support. The patient interface device 2 includes a headgear 4 and a nasal pillow assembly 6. The headgear 4 includes rigid or semi-rigid yokes 8 which provide stability to the sides of the headgear 4. In addition, the headgear 4 includes a headgear ring 9 having a seal ring 10 therein provided at the end of each yoke 8 for connecting the headgear to the nasal pillow assembly 6 as described below.

As seen most readily in FIG. 2, the nasal pillow assembly 6 includes a frame 12 made of a rigid material such as, without limitation, a plastic material, which supports a pillow sleeve 14 made of a flexible material such as, without limitation, silicone. The frame 12 includes a flange portion 16 and connector portions 18 provided at each end of the frame 12. The flange portion 16 includes vent holes 20 through which exhaled gasses may pass. The pillow sleeve 14 includes nasal prongs 22 structured to be partial received within the nares of the patient. Finally, the nasal pillow assembly 6 includes a clip 24 made of a rigid material such as, without limitation, a plastic material, the function of which is described below.

The patient interface device 2 is assembled by first assembling the nasal pillow assembly 6 by wrapping the pillow sleeve 14 around the frame 12 in a manner such that each of the lipped ends 26 of the pillow sleeve 14 is received in a space formed between respective retaining flanges 28 and the flange 16. Then, the clip 24 is slid over the flange 16 and the lipped ends 26 (FIG. 1). As seen in FIGS. 1 and 2, the clip 24 includes a rectangular opening 30 which leaves the vent holes 20 exposed when the nasal pillow assembly 6 is assembled. Next, the headgear 4 is connected to the nasal pillow assembly 6 by inserting each of the connector portions 18 of the frame 12 through a respective one of the headgear rings 9 and seals rings 10. Then, a cap 32 is inserted into one of the connector portions 18 and a tube assembly 34 having an elbow 36 is inserted into the other of the connector portions 18. The positions of the tube assembly 34 and the plug 32 may be interchanged according to preference, e.g., the typical sleeping position of the patient. The tube assembly 34 is provided with a source of pressurized gas.

Although the patient interface device 2 shown in FIGS. 1 and 2 may have advanced the art, there is still room for improvement in the field of patient interface devices. Described herein are a number of improvements to patient interface devices such as, without limitation, the patient interface device 2.

In addition, a prior version of the patient interface device 2 exists which is similar in structure to the patient interface device 2. The main difference between the two devices lies in the nasal pillow assembly of each. In particular, the nasal pillow assembly of the prior version includes a pillow sleeve that is similar to the pillow sleeve 14 of the patient interface device 2, except that it includes a series of vent holes that are provided in front of the nasal prongs thereof. In addition, unlike the frame 12 and the clip 24 of the patient interface device 2 which have one or more holes provided therein, the frame and clip of the prior version are both solid. Thus, in the prior version, exhaled gasses are passed through the vent holes of the pillow sleeve rather then through the frame and clip. Patients using the prior version often switch to the patient interface device 2, which may lead to certain problems relating component interchangeability as described elsewhere herein. In particular, patients or caregivers may attempt to use components, such as the frame and clip of one version with the remaining components of the other version, which can be problematic.

In one embodiment, the present invention provides a patient interface device that includes a frame for supporting a flexible interface member that is structured to deliver a gas to an airway of a patient, and a clip structured to be coupled to the frame by sliding the clip onto a flange provided as part of the frame. The flange includes a first element and the clip includes a second element, wherein one of the first element and the second element is structured to be received within the other of the first element and the second element when the clip is slid onto the flange to permit the clip to be fully slid onto the flange. If the first and second elements do not mate in this manner, the clip will not be able to be fully slid onto the flange. As a result, incompatible clips are discouraged from being used with the frame.

In another embodiment, the invention provides a patient interface device that includes a frame having a flange extending along a longitudinal axis of the frame, and an integrated interface assembly that includes a flexible interface member and a clip member affixed to the flexible interface member. The flexible interface member, such as a nasal pillow sleeve, is structured to deliver a gas to an airway of a patient. The flexible interface member is also structured to be at least partially wrapped around the frame and the clip member is structured to be snapped over the flange to couple the integrated interface assembly to the frame.

In yet another embodiment, the invention provides a patient interface device that includes an interface assembly structured to deliver a gas to an airway of a patient, wherein the interface assembly has an end portion which defines an opening. The patient interface device also includes an end cap having a post portion and an end portion. The post portion is received within the opening of the interface assembly and the end portion is structured to permit exhaled gases to flow therethrough.

In still another embodiment, the invention provides a patient interface device that includes an interface assembly structured to deliver a gas to an airway of a patient and that includes an end portion which defines an opening. The patient interface device further includes a tube assembly for delivering the gas to the interface assembly. The tube assembly is coupled to the interface assembly through the opening therein and includes an exhaust portion structured to permit exhaled gases to flow therethrough.

In yet another embodiment, the invention provides a patient interface device that includes a nasal pillow assembly having a frame and a flexible pillow sleeve coupled to the frame. The nasal pillow assembly is structured to deliver a gas to an airway of a patient. The patient interface device also includes a headgear coupled to the nasal pillow assembly. The headgear includes a first side yoke coupled to a first side of the frame and a second side yoke coupled to a second side of the frame. Also included is a first cheek stabilizer attached to an interior of the first side yoke and a second cheek stabilizer attached to an interior of the second side yoke.

In still a further embodiment of the invention, a patient interface device is provided that includes a nasal pillow assembly having a frame and a flexible pillow sleeve coupled to the frame, wherein the nasal pillow assembly is structured to deliver a gas to an airway of a patient. The flexible pillow sleeve has a first nasal prong, a second nasal prong, and a stabilizer provided between the first and second nasal prongs. The stabilizer is structured to engage the patient's face at a location above the patient's upper lip and below the patient's nose.

In still a further embodiment, the invention provides a patient interface device that includes a flexible nasal pillow sleeve having a first nasal prong and a second nasal prong for delivering a gas to an airway of a patient. The flexible nasal pillow sleeve includes at least one integral stiffening member. In addition, the patient interface device includes a first connecting portion attached to a first end of the flexible nasal pillow sleeve and a second connecting portion attached to a second end of the flexible nasal pillow sleeve. The first connecting portion and the second connecting portion are each structured to receive either an end cap or a tube assembly therein. The device further includes a headgear having a first yoke coupled to the first connecting portion and a second yoke coupled to the second connecting portion.

In another alternative embodiment, the invention provides a patient interface device that includes a frame having a flange, a flexible nasal pillow sleeve supported by the frame that includes first and second nasal prongs for delivering a gas to an airway of a patient, and a clip coupled to the frame by sliding the clip over the flange. The clip, when slid in this manner, couples the flexible nasal pillow to the frame. The device also includes a chin support assembly coupled to the flexible nasal pillow sleeve that is structured to support the patient's chin.

In yet another embodiment, the invention provides a patient interface device that includes a nasal pillow sleeve having a first nasal prong and a second nasal prong for delivering a gas to an airway of a patient, a tube assembly operatively coupled to the nasal pillow sleeve for delivering the gas to the nasal pillow sleeve, and a tube management device having a first end and a second end. The first end of the tube management device is coupled to the nasal pillow sleeve and is positioned between the first and second nasal prongs, and the second end of the tube management device is coupled to and supports the tube assembly. As a result, a majority of the tube assembly is positioned generally in a center of and below the nasal pillow sleeve when the device is worn by the patient.

Another embodiment provides a patient interface device that includes a nasal pillow assembly structured to deliver a gas to an airway of a patient, wherein the nasal pillow assembly includes a frame having a flange, a flexible nasal pillow sleeve supported by the frame and having first and second nasal prongs, and a clip coupled to the frame by sliding the clip over the flange. The device further includes an oral member, such as a bite block, that is coupled to the nasal pillow assembly and that is structured to be received within the patient's mouth.

In yet another embodiment, the invention provides a patient interface device that includes a nasal pillow assembly for delivering a gas to an airway of a patient, wherein the nasal pillow assembly includes a cushion portion having first and second nasal prongs that is attached to a frame portion. The device further includes a tube assembly coupled to the frame portion and in fluid communication with the nasal pillow assembly. The tube assembly is selectively slideable along the frame portion in a manner which maintains the fluid communication with the nasal pillow assembly in an airtight manner.

Therefore, it should now be apparent that the invention substantially achieves all the above aspects and advantages. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

The accompanying drawings illustrate presently preferred embodiments of the invention, and together with the general description given above and the detailed description given below, serve to explain the principles of the invention. As shown throughout the drawings, like reference numerals designate like or corresponding parts.

FIGS. 16-18 are isometric, front and rear views, respectively, of a gas deflector according to a further embodiment of the invention, and FIG. 19 is a side elevational view showing the gas deflector coupled to an end cap;

Figure 1:
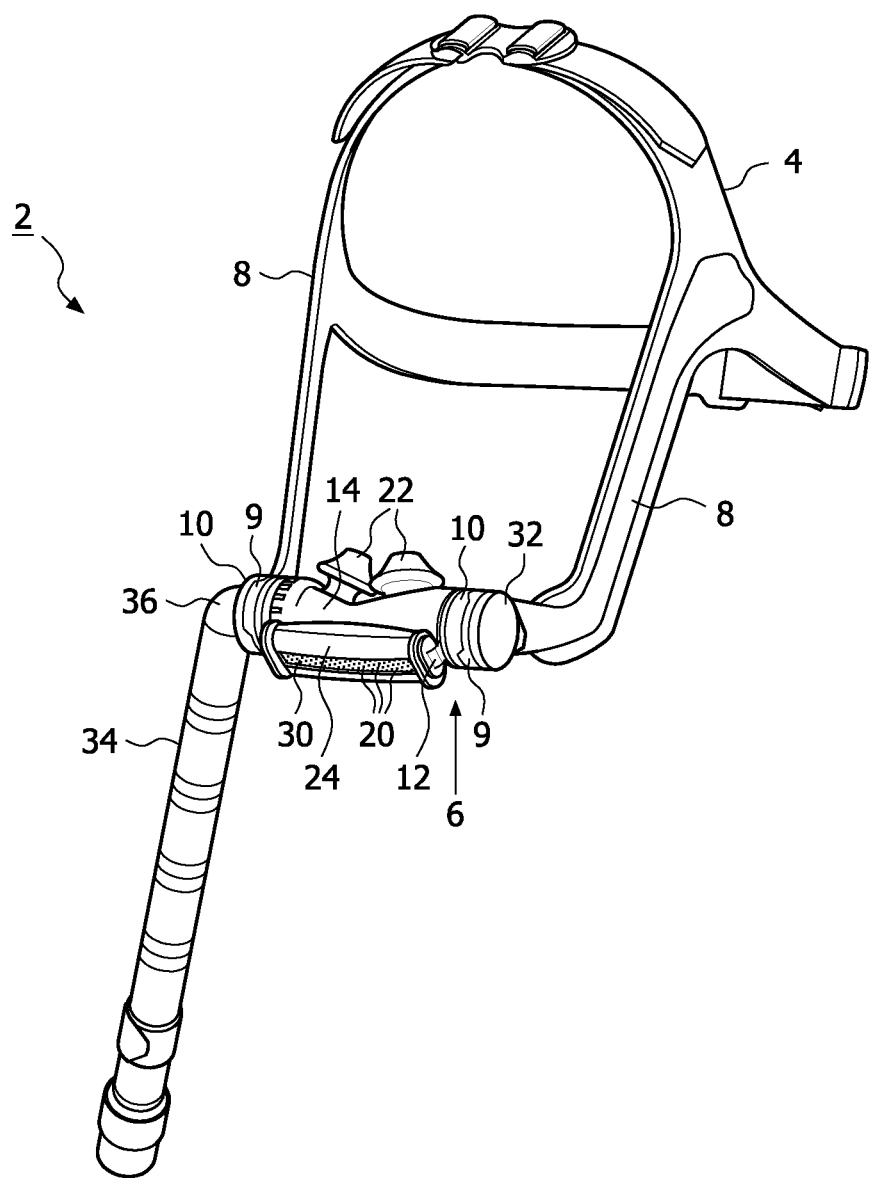
FIGS. 1 and 2 are isometric and exploded/disassembled views, respectively, of one particular prior art patient interface device.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality).

Figure 2:
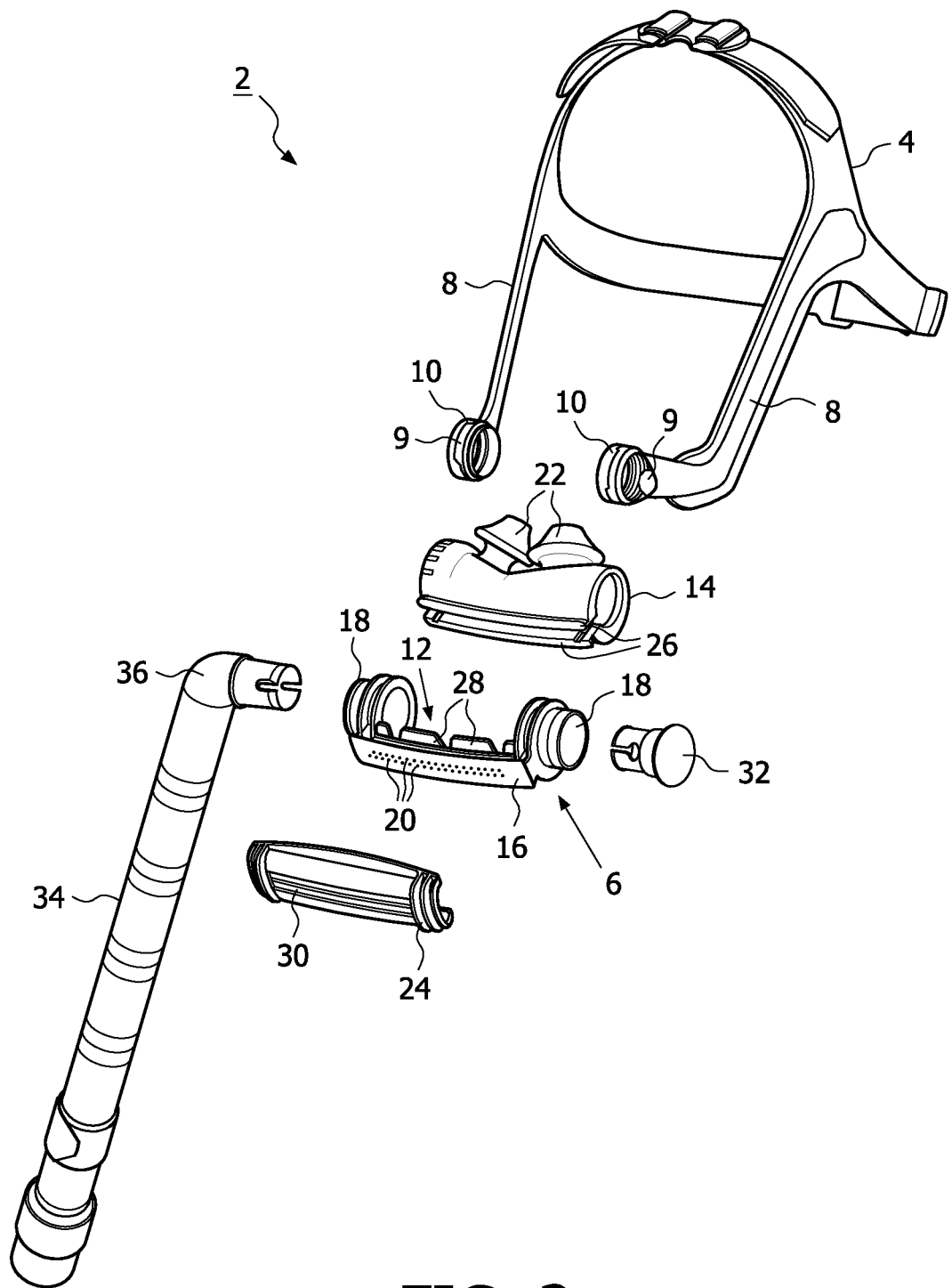

The present invention provides a number of modifications to patient interface devices employing a nasal pillow such as the patient interface device 2 shown in FIGS. 1 and 2 and/or the prior version thereof described elsewhere herein. Such modifications and/or improvements include modifications to certain of the components thereof and/or variations of the patient interface device as a whole. The various modifications and/or improvements are described in detail below in connection with FIGS. 3 through 42.

Figure 3:
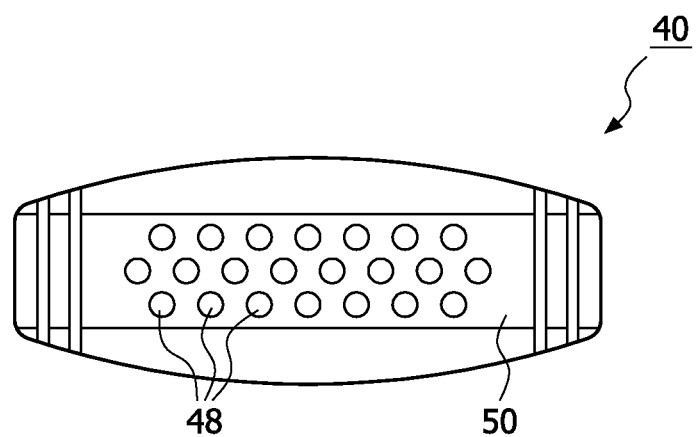
FIG. 3 is a top plan view of a clip and FIG. 4 is a top plan view of a frame according to an embodiment of the invention.
Figure 4:
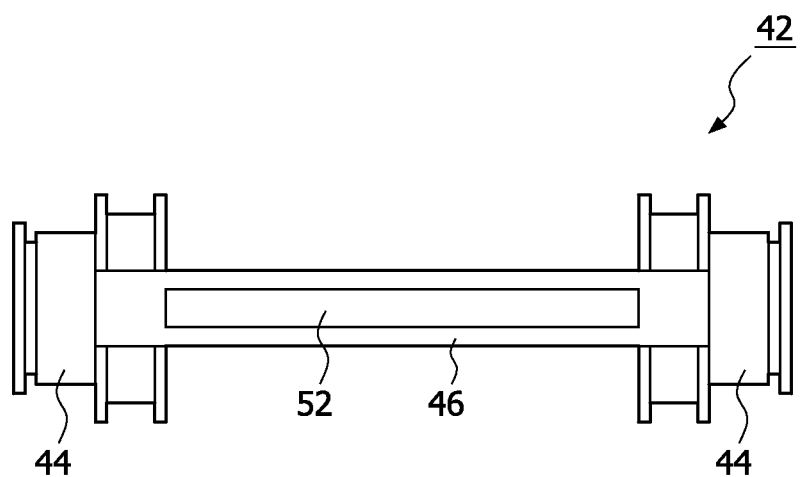

FIG. 3 is a top plan view of a clip 40 and FIG. 4 is a top plan view of a frame 42 that may be used in connection with the patient interface device 2 or a similar device as a substitute for the clip 24 and the frame 12. As seen in FIG. 4, the frame 42 includes connecting portions 44 and a flange 46. The clip 40 is structured to be slid over the flange 46 after a pillow sleeve such as, without limitation, the pillow sleeve 14 is wrapped around the frame 42 in a manner similar to the manner described in connection with the patient interface device 2. As seen in FIG. 3, the clip 40 includes a plurality of vent holes 48 provided on a top face 50 thereof. In addition, the flange 46 of the frame 42 includes a generally rectangular shaped opening 52 therein. Thus, when a nasal pillow assembly is assembled using the frame 42, the clip 40 and a pillow sleeve such as the pillow sleeve 14 shown in FIGS. 1 and 2, exhaled gasses may be vented through the vent holes 48 and the opening 52. As will be appreciated, the clip 40 may suitably be used with the pillow sleeve 14 and the clip 12 having vent holes 20 provided therein as shown in FIG. 2 and with the prior version of the patient interface device 2 which includes a pillow sleeve having vent holes provided therein and a solid frame.

Figure 5:
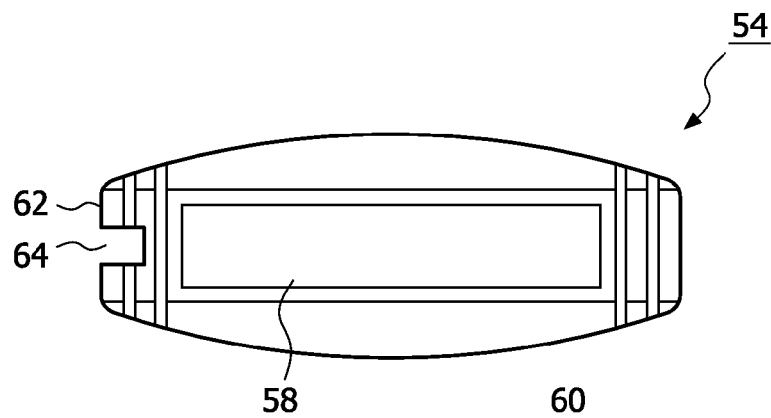
FIG. 5 is a top plan view of a clip and FIGS. 6 and 7 are side elevational and top plan views, respectively, of a frame according to another embodiment of the invention.
Figure 6:
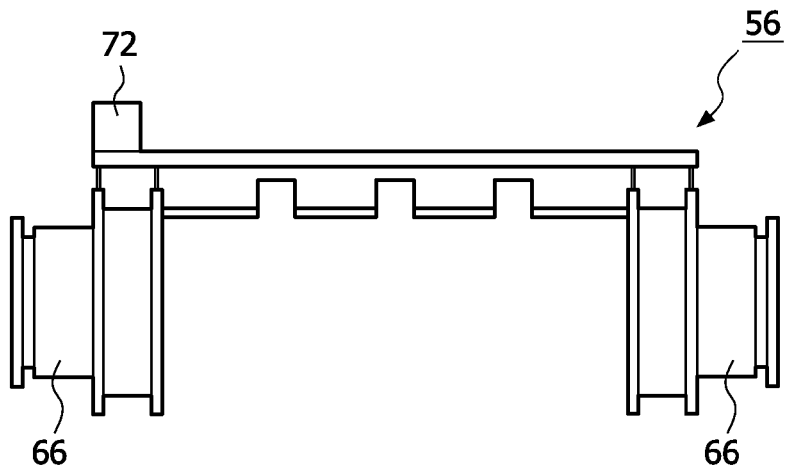
Figure 7:
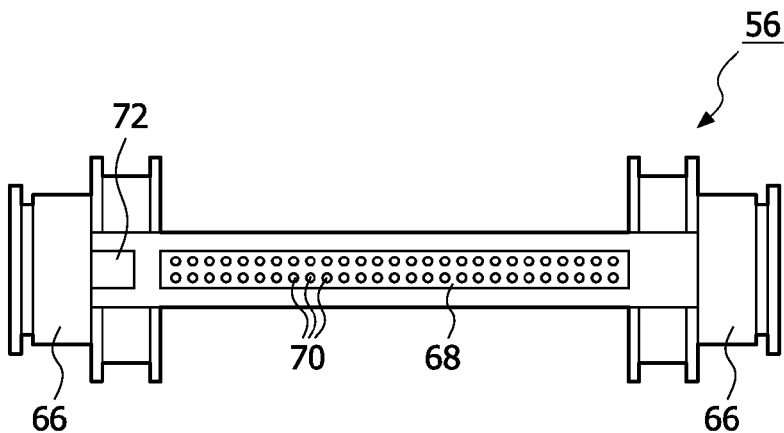

FIG. 5 is a top plan view of a clip 54 which is structured to be used in combination with a frame 56 shown in FIGS. 6 and 7. In particular, as described in more detail below, the clip 54 and the frame 56 are provided with a mechanism that ensures that only the clip 54 may be used with the frame 56 so as to avoid a mismatch of components. As seen in FIG. 5, the clip 54 includes a generally rectangularly shaped opening 58 provided on a front face 60 thereof. Alternatively, the opening 58 may be replaced with a plurality of vent holes similar to the vent holes 48 shown in FIG. 3. In addition, a first end 62 is provided with a generally rectangularly shaped notch 64. Referring to FIGS. 6 and 7, the frame 56 includes connector portions 66 and a flange 68 having a plurality of vent holes 70 provided therein. Alternatively, the vent holes 70 may be replaced by a generally rectangularly shaped opening similar to the opening 52 shown in FIG. 4. In addition, the flange 68 has a generally rectangularly shaped post 72 extending from a top surface thereof. The shape of the post 72 is structured to match the shape of the notch 64. Thus, when the clip 54 is slid onto the flange 68 after a pillow sleeve such as a pillow sleeve 14 has been wrapped around the clip 56, the post 72 will be received within the notch 64 so that the clip 54 may be slid all the way in place on the frame 56. As will be appreciated, if a clip not having a notch 64 is attempted to be slid onto the frame 56, it will not be able to be slid completely thereon due to interference provided by the post 72. As a result, the provision of the notch 64 and the post 72 ensure that only the clip 54 (or a similarly structured clip) may be properly slid onto the flange 68 during the assembly of a patient interface device that incorporates the frame 56, thereby preventing a mismatch of components (i.e., the use of another, non-matching clip).

Figure 8:
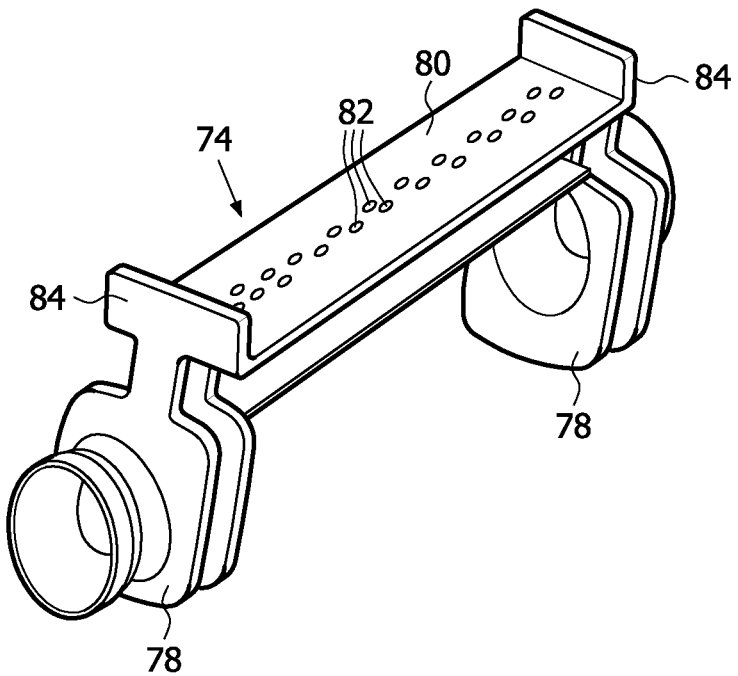
FIG. 8 is an isometric view of a clip and FIG. 9 is an isometric view of an integrated pillow sleeve assembly according to another embodiment of the invention.
Figure 9:
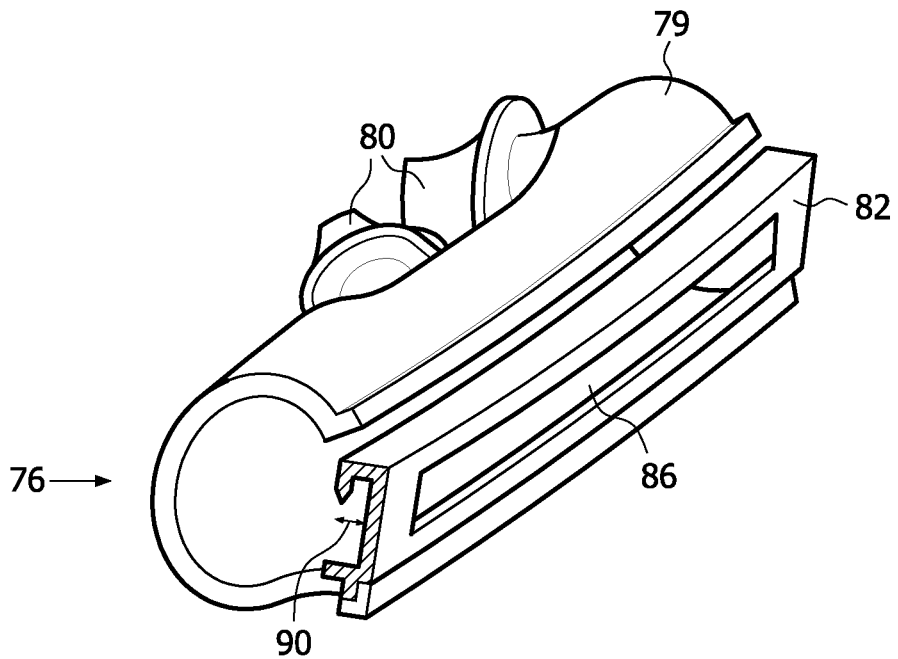

FIG. 8 is an isometric view of a clip 74 structured to be used in conjunction with an integrated pillow sleeve assembly 76 as shown in FIG. 9. The frame 74 is similar to the frame 12 shown in FIGS. 1 and 2 in that it includes connector portions 78 and a flange 80 having a plurality of vent holes 82 provided therein. One problem that is associated with the frame 12 shown in FIGS. 1 and 2 is that a solid clip, such as the clip provided with the prior version of the patient interface device 2 described elsewhere herein, may also be used in combination with the frame 12. This presents a potentially dangerous condition because if the pillow sleeve 14, which does not include any vent holes therein, is wrapped around the frame 12 and a prior solid clip is used instead of the clip 24 shown in FIGS. 1 and 2, the resulting assembly will not include any means for escape of exhalation gases as the solid clip will close and cover the vent holes 20 provided in the frame 12. Thus, when a pillow sleeve such as the pillow sleeve 14 not having vent holes provided therein is intended to be used with a frame having vent holes provided therein, it is desirable to provide a mechanism which prevents the improper use of a non-compatible clip such as a solid clip therewith.

Figure 10:
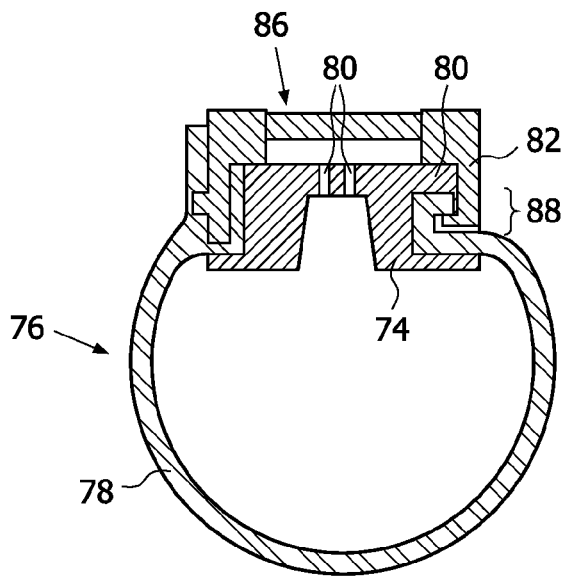
FIG. 10 is a cross-sectional view of the clip of FIG. 9 coupled to the frame of FIG. 8.

The use of such an improper clip is discouraged according to one embodiment of the present invention by providing the integrated pillow sleeve member 76 shown in FIG. 9. In particular, the integrated pillow sleeve member 76 includes a pillow sleeve portion 79 which includes nasal prongs 80 and which is similar in structure to the pillow sleeve 14 shown in FIGS. 1 and 2. However, the integrated pillow sleeve member 76 also includes an integral clip member 82 that is provided as a part thereof. The integral clip member 82 may be affixed to the pillow sleeve portion 79 to form the integrated pillow sleeve member 76 in any of a number of known manners. For example, and without limitation, the pillow sleeve portion 79 may be over molded onto the clip member 82, the pillow sleeve portion 79 may be affixed to the clip member 82 by an adhesive (such as a glue material), or the pillow sleeve portion 78 may be affixed to the clip member 82 by a suitable mechanical attachment mechanism. During assembly, the integrated pillow sleeve member 76 is wrapped around the frame 74 in a manner such that the clip member 82 is received between the upstanding end portions 84 of the clip 74 and is snapped over the flange 80 as shown in FIG. 10, which is a cross-sectional view showing the integrated pillow sleeve member 76 and a frame 74 assembled together. The clip member 82 of the integrated pillow sleeve member 76 includes a generally rectangular shaped opening 86 which, in combination with the vent holes 82 of the frame 74, allows exhaled gasses to escape from a patient interface device that incorporates the assembly shown in FIG. 10. Because the clip 74 and the integrated pillow sleeve member 76 requires the clip member 82 to be snapped over the flange 80 of the frame 74, users will not think about using a sliding member in any patient interface device that includes these components. Thus, as a result, it is unlikely that a user will mistakenly try to use a solid clip in any patient interface device intended to employ the clip 74. In addition, the upstanding end portions 84 further discourage the use of a sliding clip with the frame 74. In particular, if the height of the upstanding end portions 84 is made large enough (larger than the height of the non-compatible clip), the non-compatible clip will not be able to be slid over the flange 80 even if a user were to attempt to do so. Furthermore, the ability to snap a non-compatible clip such as a solid clip over the flange 80 may be limited by making the dimension 88 shown in FIG. 10 larger than the internal height of such an incompatible clip (as a result, even if attempted, the clip will not be able to be snapped over the flange 80 when a pillow sleeve such as pillow sleeve 14 is wrapped thereover). As a result, any or all of these mechanisms help to ensure that only the integrated pillow sleeve member 76 will be used in connection with the frame 74, thereby avoiding potentially dangerous combinations of incompatible components. In addition, it would be undesirable and potentially dangerous for the integrated pillow sleeve member 76 to be used with a solid frame as described elsewhere herein that does not include any vent holes or openings as such a combination would provide no means for exhaled gasses to escape. Therefore, it is desirable to make the integrated pillow sleeve member 76 in a manner that would discourage its use with such a frame. This may be done by making the internal height of the clip member 82 small enough such that it cannot be fit over the flange of the incompatible frame. The internal height is shown in FIG. 9 with reference numeral 90.

Figure 11:
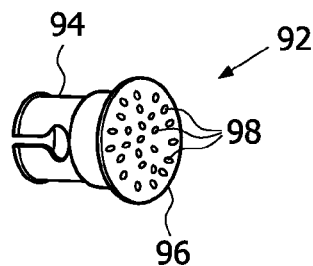
FIG. 11 is an isometric view of an end cap according to one particular embodiment.
Figure 12:
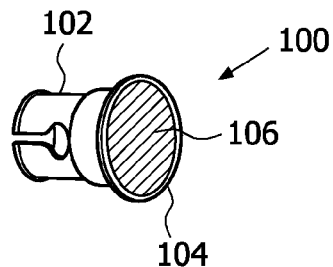
FIG. 12 is an isometric view of an end cap according to another particular embodiment.

As described elsewhere herein, the patient interface device 2 shown in FIGS. 1 and 2 employs a cap 32 which is structured to be inserted through the headgear ring 9, the seal ring 10, and the connector portion 18 when the patient interface device 2 is assembled. FIG. 11 is an isometric view of an end cap 92 according to one embodiment of the present invention. The end cap 92 includes a hollow post portion 94 that is adapted to be received within a connector portion such as, without limitation, a connector portion 18 of the patient interface device 2 (and through the headgear ring 9 and seal ring 10 thereof). The end cap 92 also includes an end portion 96 attached to the post portion 94. The end portion 96 includes a plurality of vent holes 98 provided therein which are in fluid communication with the interior of the post portion 94. Thus, when the end cap 92 is inserted into a connector portion such as the connector portion 18 of the patient interface device 2, patient exhaled gasses are able to vented through the vent holes 98. As will be appreciated, use of the end cap 92 allows the remaining portions of the patient interface device with which it is used to be solid (i.e., do not have any vent holes or openings therein). In particular, the end cap 92 may be used with the pillow sleeve 14 shown in FIGS. 1 and 2 in conjunction with a solid frame and a solid clip (i.e., from the prior version), because the end cap 92 provides the means through which patient exhaled gasses may escape. FIG. 12 is an isometric view of an alternative end cap 100 according to an alternative embodiment of the invention. The end cap 100 includes a hollow post portion 102 and an end portion 104. The end portion 104 is made at least partially from a porous material 106 that allows gasses to be passed from the interior of the post portion 102 through the end portion 104. The porous material or media 106 may be, for example, porous Polypropylene, porous High Density Polyethylene (HDP), porous Ultra-High Molecular Weight Polyethylene (UHMWP), porous PTFE, porous PDDF, or other suitable porous materials. Example suitable materials are available from Porex Corporation of Fairburn, Ga. Any suitable porous membrane product will be acceptable.

Figure 13:
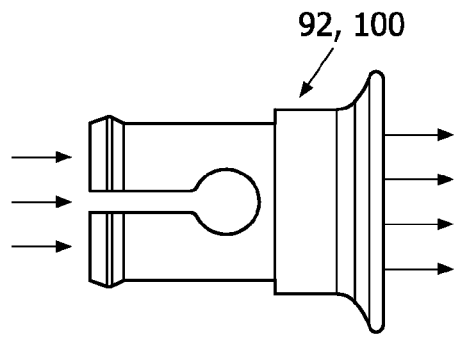
FIG. 13 is a side elevational view demonstrating airflow through the end caps shown in FIGS. 11 and 12.

FIG. 13 demonstrates the direction of flow of exhalation gasses when either the end cap 92 or the end cap 100 is employed in patient interface device such as, without limitation, the patient interface device 2.

Figure 14:
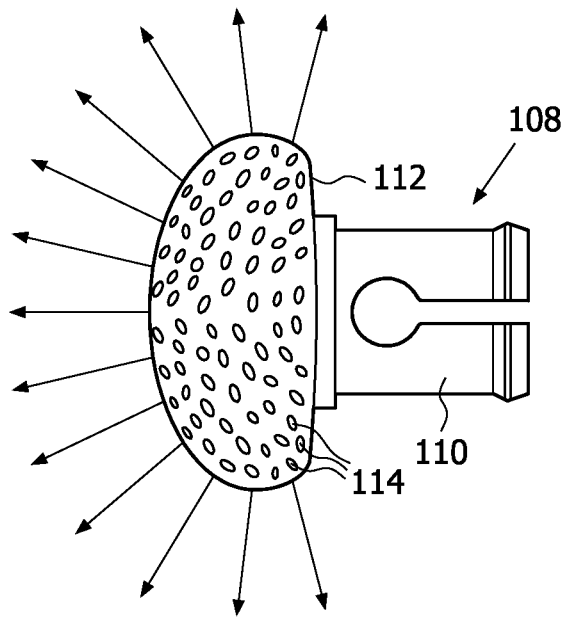
FIG. 14 is a side elevational view and FIG. 15 is an isometric view of an end cap according to an alternative embodiment.
Figure 15:
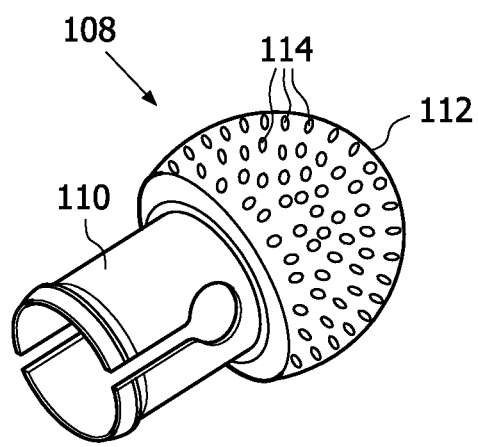

FIG. 14 is a side elevational view and FIG. 15 is an isometric view of an end cap 108 according to a further alternate embodiment of the present invention. The end cap 108 includes a hollow post portion 110 and a bulbous end portion 112. The end portion 112 includes a plurality of vent holes 114 that are in fluid communication with the interior of the post portion 110 in order to allow exhaled gasses to pass from the interior of the end portion 110 through the vent holes 114. The bulbous nature of the end portion 112 provides for improved diffusion of gas flow as compared to the end portions 96 and 104 shown in FIGS. 11 and 12. In particular, the flow of exhalation gasses, as shown in FIG. 14, is directed in a number of directions that intersects the longitudinal axis of the post portion 110. In fact, in the embodiment shown in FIG. 14, exhaled gasses are, as indicated by the arrows, able to flow in a hemispherical pattern over a span of more than 180 degrees with respect to the longitudinal axis of the end portion 110. This is in contrast to the flow of exhaled gasses shown in FIG. 13, which flow is substantially parallel to the longitudinal axis of the post portion 94,102, as the case may be. As a result, the flow of exhaled gasses when the end cap 108 is employed is not as concentrated in a particular direction as in when end cap such as end cap 92 or 100 is used. Such a concentrated flow of exhaled gasses can, in some circumstances, be problematic as it may be undesirably directed at, for example, the patient's ear or at the bed partner of the patient.

FIGS. 16, 17 and 18 are isometric, front elevational, and rear elevational views of an embodiment of a gas deflector 116 according to a further aspect of the present invention. As seen in FIG. 16-18, the gas deflector 116 includes a deflector body 118, and legs 120 which define a receiving slot 122. As shown in FIG. 19, the gas deflector 116 is structured to be mounted on an end cap such as end cap 92 or 100 in order to advantageously deflect the exhaled gasses being emitted through the end cap 92,100 in a desired direction as indicated by the arrows shown in FIG. 19. In particular, the end of the post portion 94,102 is structured to be received within the receiving slot 122 of the gas deflector 116. When so received, the legs 120 will be positioned between the end portion 98,104 and the connecting portion of a frame in which it is inserted. The gas deflector 116 may be selectively positioned about the outer periphery of the end cap 92,100 in order to cause the deflector body 118 to selectively deflect the flow of gas in a desired direction. As a result, the flow of gas may be selectively directed away from a body part of the patient, such as the patient's ear, and/or the patient's bed partner.

Figure 20A:
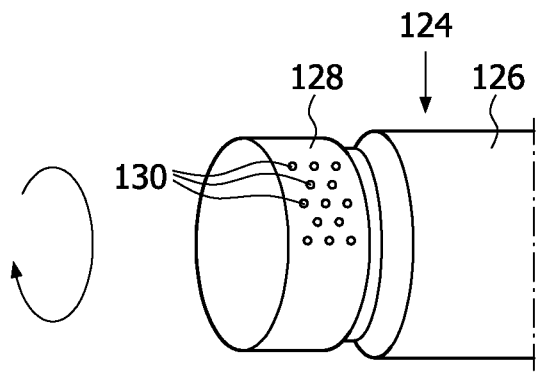
FIGS. 20A and 20B are isometric and side elevational views, respectively, of an end cap according to still a further embodiment of the invention.
Figure 20B:
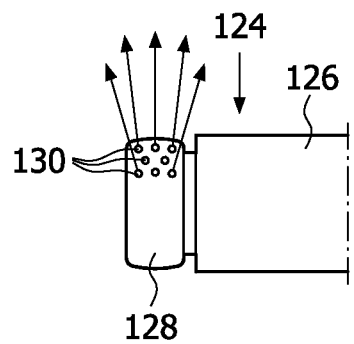
Figure 21A:
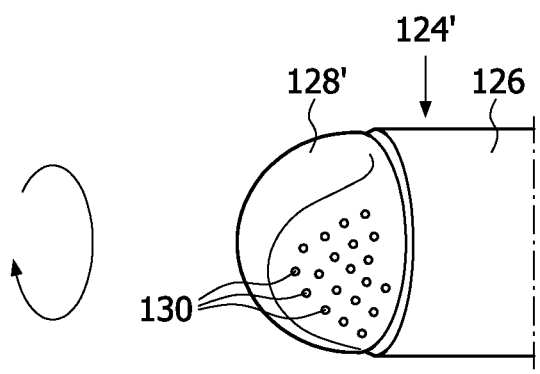
FIGS. 21A and 21B are isometric and side elevational views, respectively, of an end cap according to yet a further alternative embodiment of the invention.
Figure 21B:
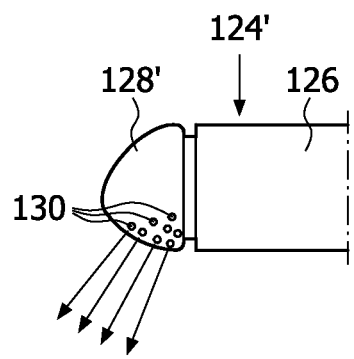

FIGS. 20A and 20B show an alternative end cap 124 according to an alternative embodiment of the present invention. The alternative end cap 124 includes a first portion 126 structured to be received within a connecting portion of a frame, such as the connecting portion 118 of the frame 12 or any other connecting portion of a frame described elsewhere herein. A rotatable end portion 128 is rotatably attached to the post portion 126 in a manner which allows the end portion 128 to be selectively located relative to the longitudinal axis of the post portion 126 while maintaining an airtight seal between the end portion 128 and the post portion 126. The end portion 128 is provided with a plurality of vent holes 130 along a selected, limited portion thereof. The vent holes 130 are in fluid communication with the interior of the post portion 126 and allow exhaled gasses to flow from the interior of the post portion 126 through the vent holes 130. A user, by selectively locating the end portion 126, is able to selectively direct the direction of flow of the exhaled gas as shown in FIG. 20B. In the embodiment shown in FIGS. 20A and 20B, the end portion 128 has a generally cylindrical shape. FIGS. 21A and 21B show an alternative embodiment of an end cap 124' which is similar to the end cap 124 except that the end portion 128' of the end cap 124' is generally dome shaped. Like the end portion 128, the end portion 128' of the end cap 124' is able to be selectively rotated in order to selectively direct the flow of exhaled gas as shown in FIG. 21B.

Figure 22:
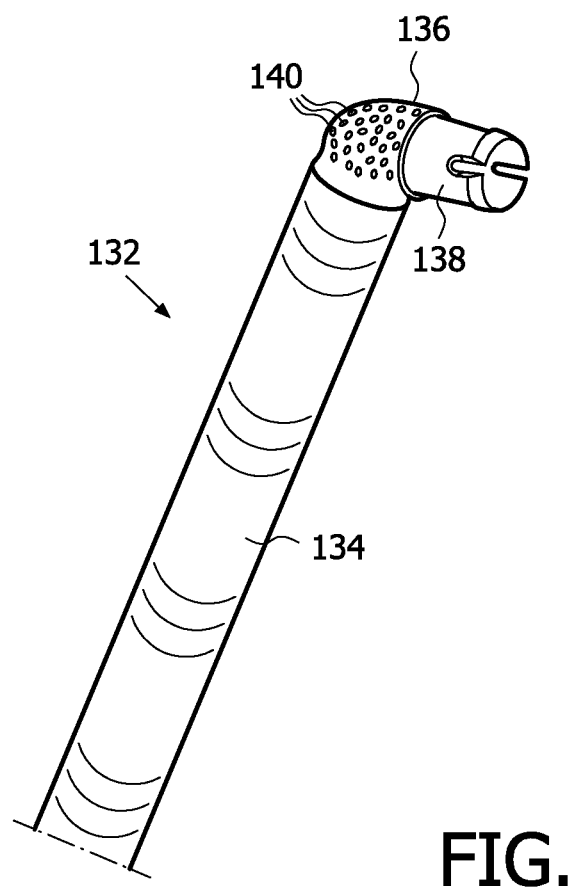
FIG. 22 is an isometric view of a tube assembly according to a further embodiment of the invention.

Referring to FIG. 22, an isometric view of a tube assembly 132 according to a further embodiment of the present invention is shown. The tube assembly 132 includes a gas delivery tube 134, and elbow portion 136, and a post portion 138 which is adapted to be received within a connecting portion of frame, such as the connecting portion 18 of the frame 12 or another connecting portion of a frame described elsewhere herein. As seen in FIG. 22, the elbow portion 136 of the tube assembly 132 includes a plurality of vent holes 140. The vent holes 140 are in fluid communication with the interior of the post portion 138 and allow exhaled gasses to pass therethrough. As a result, as was the case with the end caps 92,100, 108,124 and 124', the elbow portion 136 may be used with a pillow sleeve, a frame, and a clip that are solid and contain no vent holes.

Figure 23:
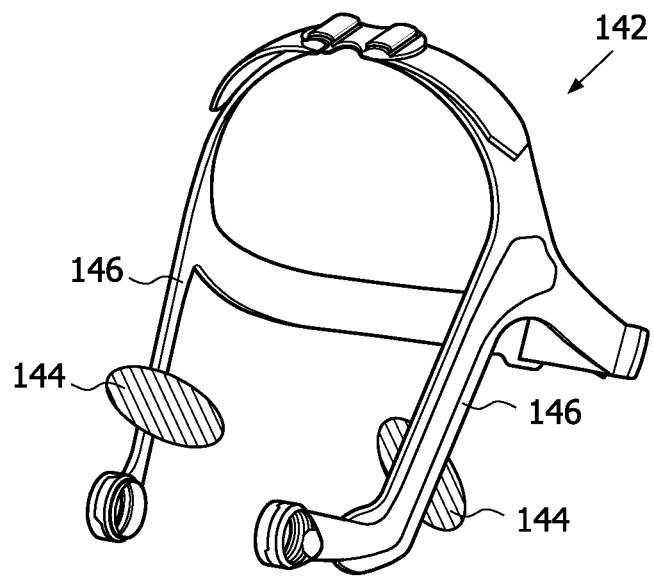
FIG. 23 is an isometric view of a headgear according to yet another alternative embodiment.

Referring to FIG. 23, a headgear 142 according to a further embodiment of the present invention is shown. The headgear 142 is similar to the headgear 4 shown in FIGS. 1 and 2, except that it includes cheek stabilizers 144 on the interior of the yokes 146 thereof. Preferably, the cheek stabilizers 144 are in the form of a soft pad such as, without limitation, a silicone gel or polyurethane gel pad. When the headgear 142 is worn by a patient, the cheek stabilizers 144 are structured to be in contact with the patient's cheeks in order to stabilize the headgear 142 in place and reduce the strapping forces that are necessary to hold a nasal pillow assembly such as a nasal pillow assembly 6 or any other suitable nasal pillow assembly as described herein in place. Preferably, as shown in FIG. 23, the cheek stabilizers 144 have a circular or oblong disc shape.

Figure 24:
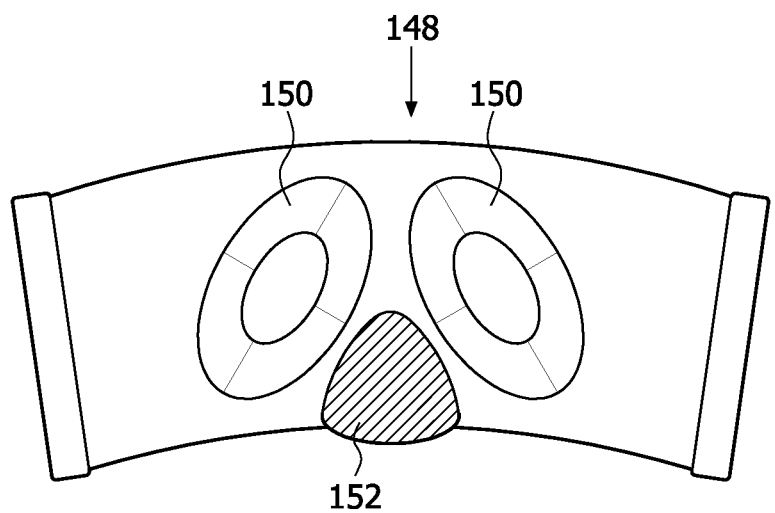
FIG. 24 is a top plan view.
Figure 25:
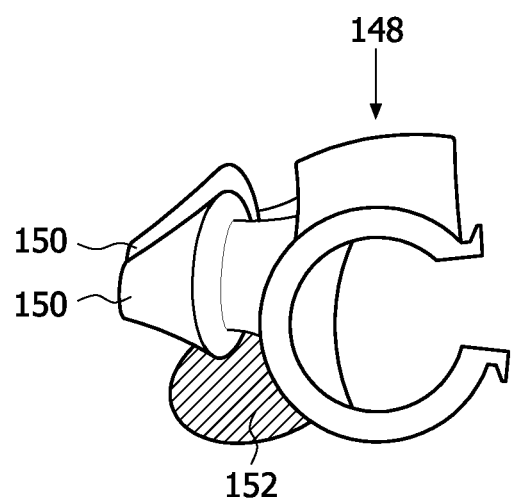
FIG. 25 is a side elevational view of a pillow sleeve according to yet another embodiment of the invention.

FIG. 24 is a top plan view and FIG. 25 is a side elevational view of a pillow sleeve 148 according to yet another embodiment of the present invention that may be used in connection with a frame and clip as described herein, such as, without limitation, the frame 12 and the clip 24 shown in FIGS. 1 and 2. The pillow sleeve 148 shown in FIGS. 24 and 25 includes nasal prongs 150 and an upper lip stabilizer 152 provided between and below the nasal prongs 150. Preferably, the upper lip stabilizer comprises a soft pad made from, for example, a silicone gel or polyurethane gel material. Using either/or cheek stabilizers 144 and the upper lip stabilizer 152 may allow the rigid portions of the yokes 146 to be eliminated, thereby allowing the entire headgear 142 to be made of a soft, flexible material. The upper lip stabilizer is structured to be positioned beneath the nose and above the upper lip when an assembly employing the pillow sleeve 148 is worn.

Figure 26:
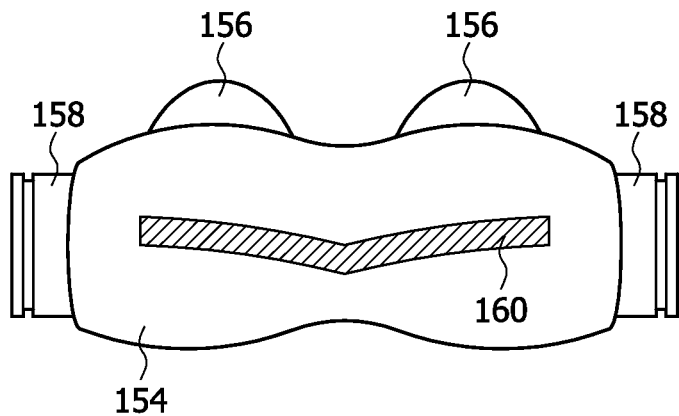
FIGS. 26, 27 and 28 are front elevational views of various embodiments of a bendable and formable pillow sleeve according to a further aspect of the invention.
Figure 27:
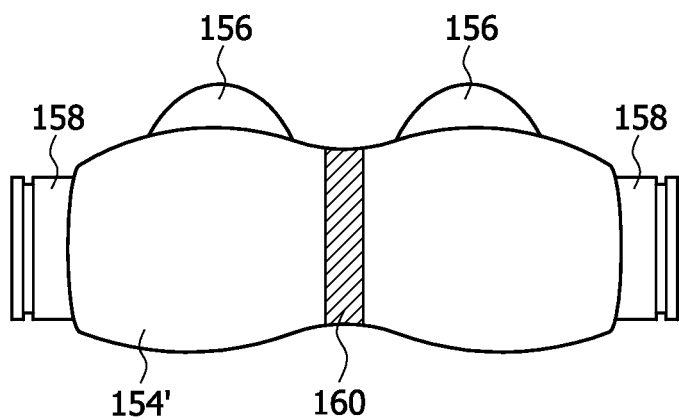
Figure 28:
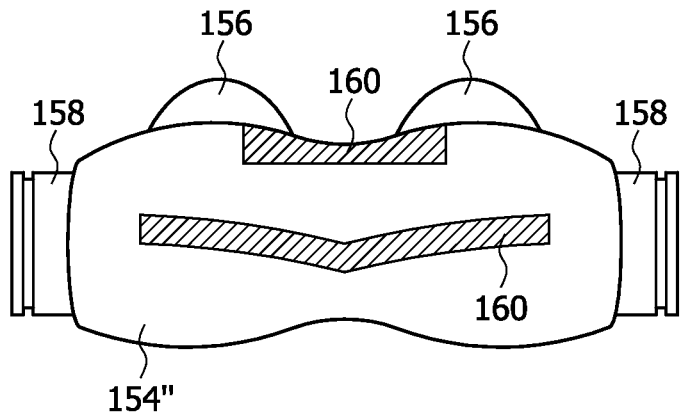

FIGS. 26, 27 and 28 shows various embodiments of a pillow sleeve that is bendable and formable according to a further aspect of the invention. The pillow sleeves shown in FIGS. 26, 27 and 28 may be utilized without a frame and a slide, such as the frame 12 and the slide 24. In particular, FIG. 26 shows a pillow sleeve 154 that includes nasal prongs 156 and connecting portions 158 attached thereto. In addition, the pillow sleeve 154 further includes an integrated stiffening member 160 that is preferably bendable and formable. The stiffening member may be, for example and without limitation, a metal or plastic material that is over molded with the pillow sleeve 154, attached to the pillow sleeve 154 using a suitable adhesive, or inserted within a pocket provided in the pillow sleeve 154. The connecting portions 158 are preferably made of a rigid material and may be over molded with the pillow sleeve 154, attached to the pillow sleeve 154 with a suitable adhesive, or otherwise attached to the pillow sleeve 154 using a suitable mechanical attachment mechanism. The connecting portions 158 are structured to be able to receive any one of the end caps 32,92,100,124 or 124'. In addition, the connecting portions 158 are also structured to be able to receive the tube assembly 34 or the tube assembly 132 shown in FIG. 22. The stiffening member 160, in addition to providing sufficient rigidity to eliminate the need for a frame and a slide, also makes the nasal pillow 154 bendable and formable so as to be able to custom adjust the angle of the nasal prongs 156. FIG. 27 is an alternate embodiment of a pillow sleeve 154 that includes a vertically oriented stiffening member 160, and FIG. 28 is an embodiment of a pillow sleeve 154" that includes multiple stiffening members 160.

Figure 29:
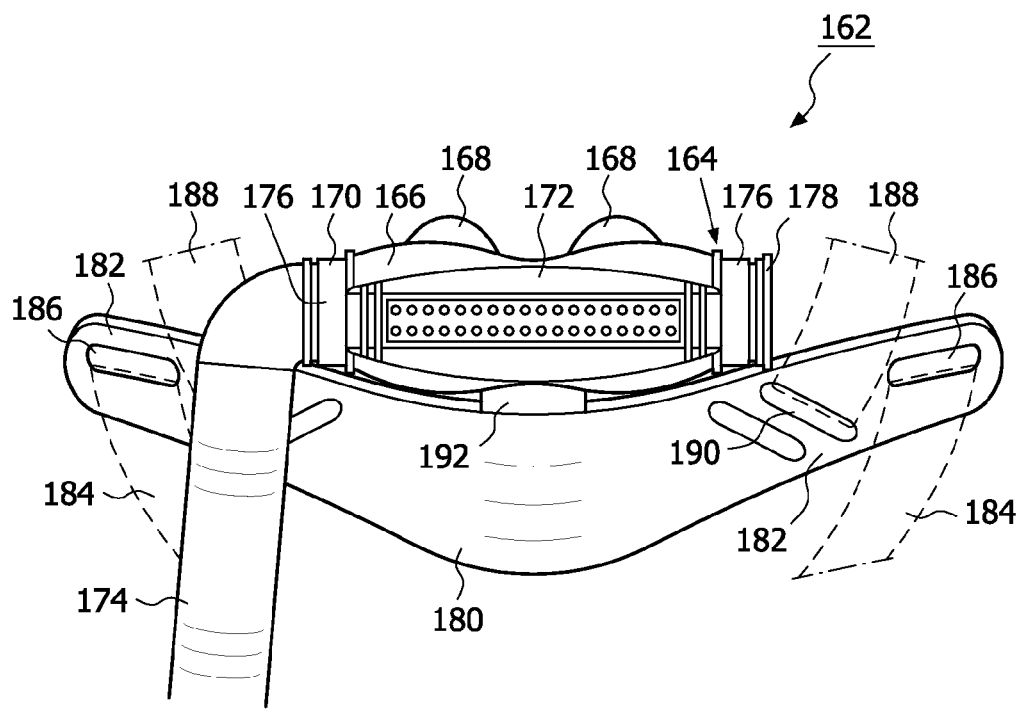
FIG. 29 is a front elevational view and FIG. 30 is a side elevational view of a patient interface device according to a further embodiment of the invention.
Figure 30:
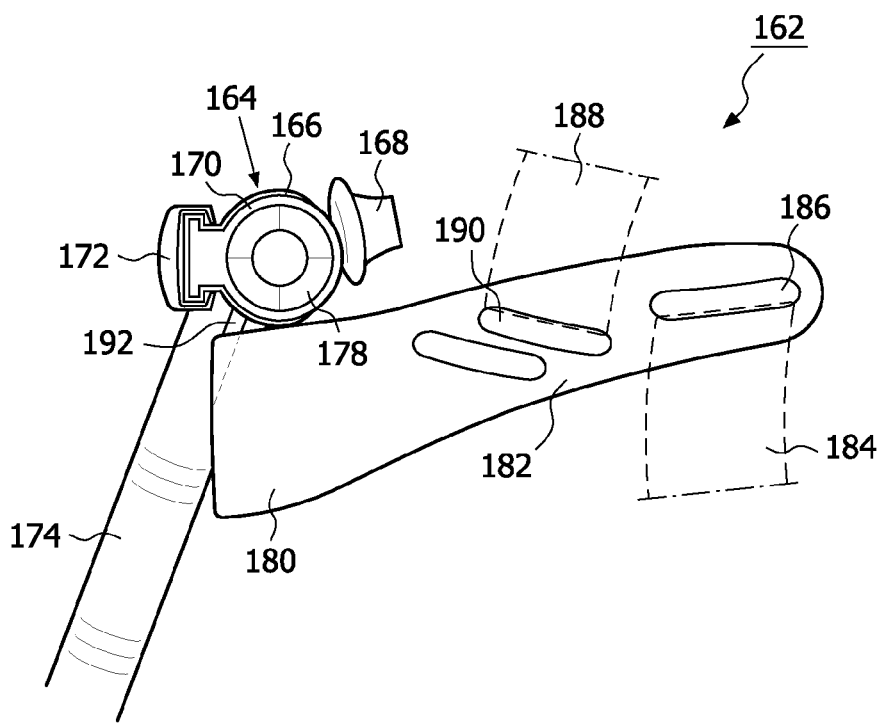

FIG. 29 is a front elevational view and FIG. 30 is a side elevational view a patient interface device 162 according to a further embodiment of the invention. The patient interface device 162 includes, in the particular embodiment shown, a nasal pillow assembly 164 that is similar to the nasal pillow assembly 6 shown in FIGS. 1 and 2. The nasal pillow assembly 164 includes a pillow sleeve 166 having nasal prongs 168, a frame 170, and a clip 172. Although a frame 170 and a clip 172 similar to the frame 12 and clip 24 shown in FIGS. 1 and 2 are shown in this particular embodiment, it should be understood that this is not meant to be limiting and that other frames and/or clips as described elsewhere herein may be used as desired. A tube assembly 174 is inserted within a connecting portion 176 of the frame 170 and an end cap 178 is inserted within the other connecting portion 176 of the frame 170. The end cap 178 may either similar to the end cap 32 shown in FIGS. 1 and 2, or any of the end caps 92,100,108,124 or 124'. In addition, the patient interface device 162 includes a chin support assembly 180 including a rigid body having arms 182. A chin support strap 184 is inserted through a pair of apertures 186 for supporting the chin of the patient, and a headgear strap 188 is inserted through apertures 190 and is structured to wrap around the head of the patient to help support the patient interface device 162. The nasal pillow assembly 164 is attached to the chin support assembly 180 by way of a rigid connector 192. Preferably, the rigid connector is molded as part of the body of the chin support assembly 180 and is attached to the pillow sleeve 166 of the nasal pillow assembly 164 using a suitable mechanism, such as over molding, an adhesive, or some other mechanical attachment mechanism. As seen in FIGS. 29 and 30, gas is delivered to the patient interface device 162 through the tube assembly 174 in a manner similar to the manner in which gas is delivered to the patient interface device 2 through the tube assembly 34 shown in FIGS. 1 and 2. In an alternative embodiment, the chin support strap 184 may be replaced by a rigid chin support member that forms a part of the chin support assembly 180.

Figure 31:
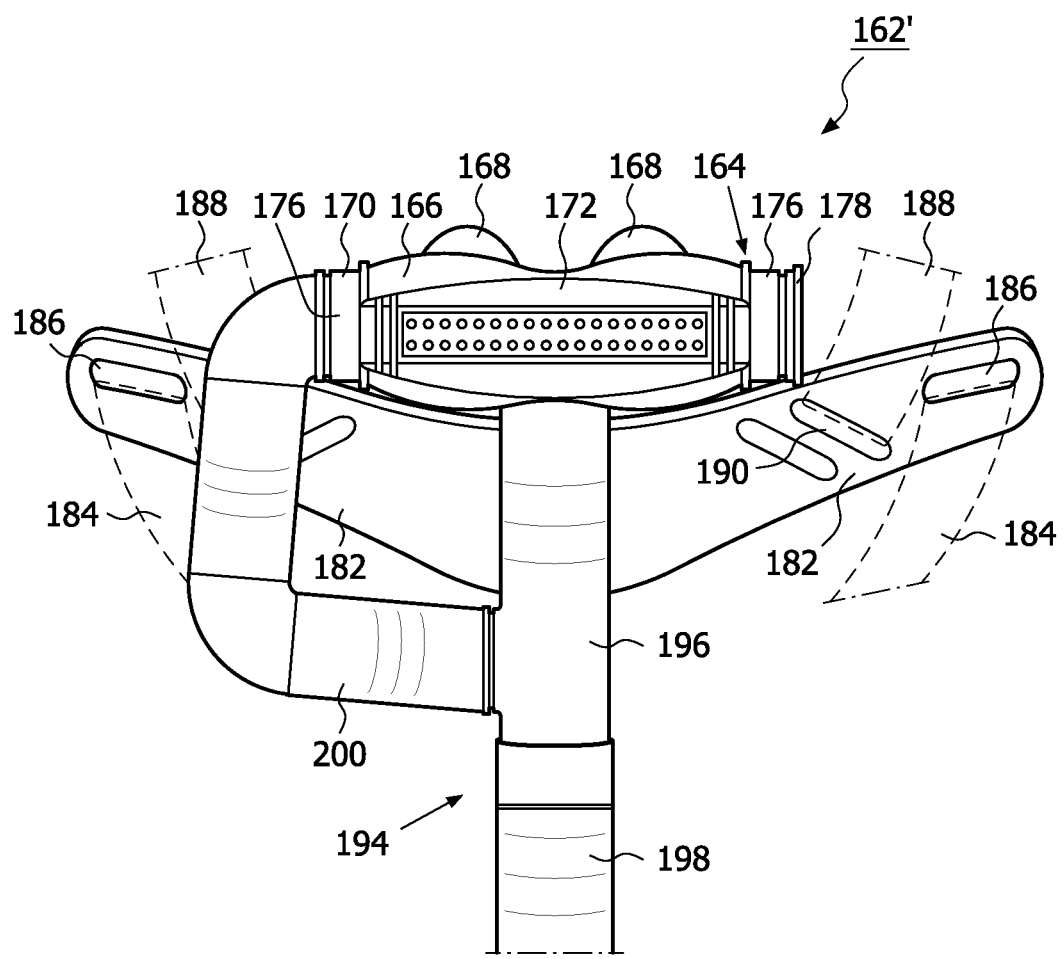
FIG. 31 is a front elevational view and FIG. 32 is a side elevational view of a patient interface device according to yet another alternative embodiment.
Figure 32:
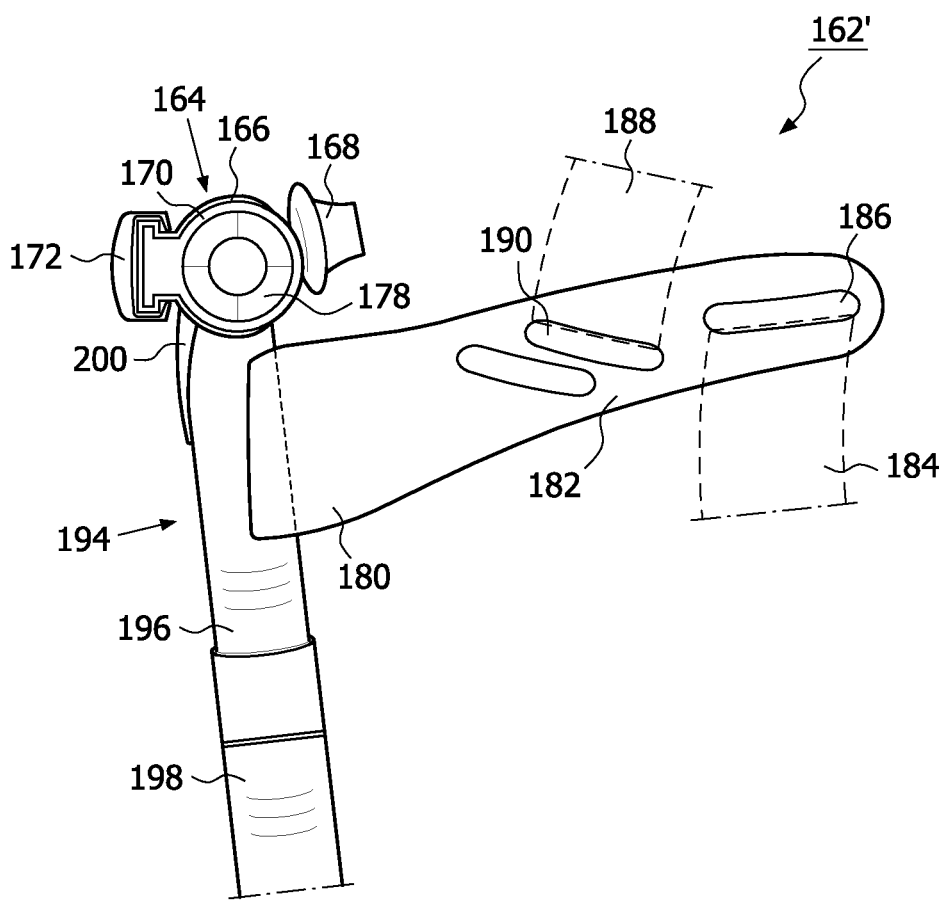

FIG. 31 is a front elevational view and FIG. 32 is a side elevational view of a patient interface device 162' that is similar to the patient interface device 162 shown in FIGS. 31 and 32, except that instead of gas being delivered thereto by way of a tube assembly 174 that is similar to the tube assembly 34, gas is delivered thereto by a tube assembly 194 that includes a rigid main tube and support mechanism 196 that is connected to a main supply tube 198, and a tube assembly branch 200 which is in fluid communication with the main tube and support mechanism 196 at one end thereof and the nasal pillow assembly 164 at the opposite end thereof. As seen in FIG. 32, in this embodiment of the patient interface device 162', arms 182 extend from the main tube and support mechanism 196.

Figure 33:
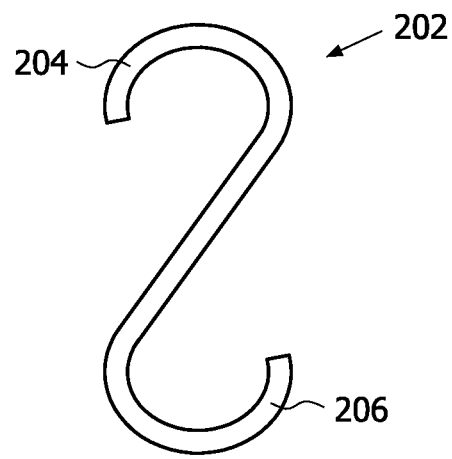
FIG. 33 is a side elevational view of a tube management device according to yet another embodiment of the invention.
Figure 34:
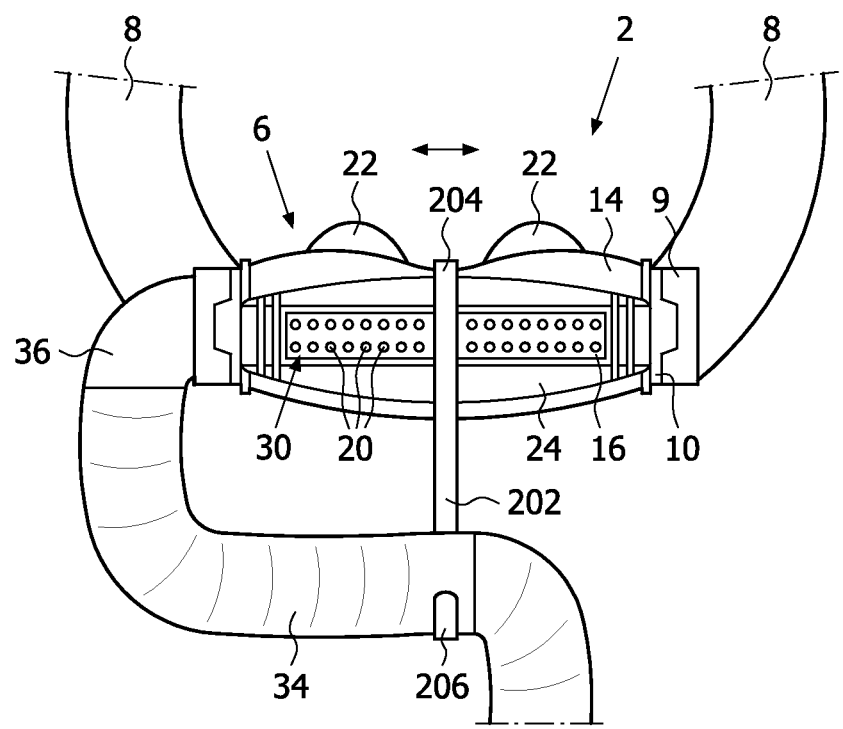
FIG. 34 is a front elevational view of a patient interface device which incorporates the tube management device shown in FIG. 33.

As noted elsewhere herein, when a patient assembles the patient interface device 2 shown in FIGS. 1 and 2, the patient must decide on which side to place the tube assembly 34. Typically, the patient uses one side or the other depending upon which side of the body the user prefers to sleep on. As will be appreciated, once the user makes this choice and places the patient interface device 2 on his or her head, the user's ability to sleep on the other side of his or her body is limited (the tube assembly 34 will get in the way if the user switches to sleeping on the other side). FIG. 33 is a side elevational view of a tube management device in the form of an S-shaped hook 202 which enables a patient to simply and easily position the tube assembly 34 in the center of his or her body. The hook 202 includes a first end 204 and a second end 206. Preferably, the hook 202 is made from a rigid or semi-rigid material such as, without limitation, metal or plastic. As seen in FIG. 34, the user hooks the first end 204 around the center of the nasal pillow assembly 6 in between the nasal prongs 22. The user then positions the tube assembly 34 so that it is supported by the second end 206 of the hook 202. As seen in FIG. 34, this will result in the majority of the tube assembly 34 being positioned generally in the center of and below the patient interface device 2 and therefore in the center of the patient's body when the patient interface device 2 is worn by the patient. As shown by the arrows in FIG. 34, the hook 202 may be selectively slid from side-to-side on the nasal pillow assembly 6 in order to selectively position the hook 202 and therefore the tube assembly 34. Furthermore, although the hook 202 has been demonstrated in connection with the patient interface device 2, it should be understood that this is meant to be exemplary only, and not limiting, and that the hook 202 may be used in connection with other patient interface device embodiments such as the various embodiments described elsewhere herein.

Figure 35:
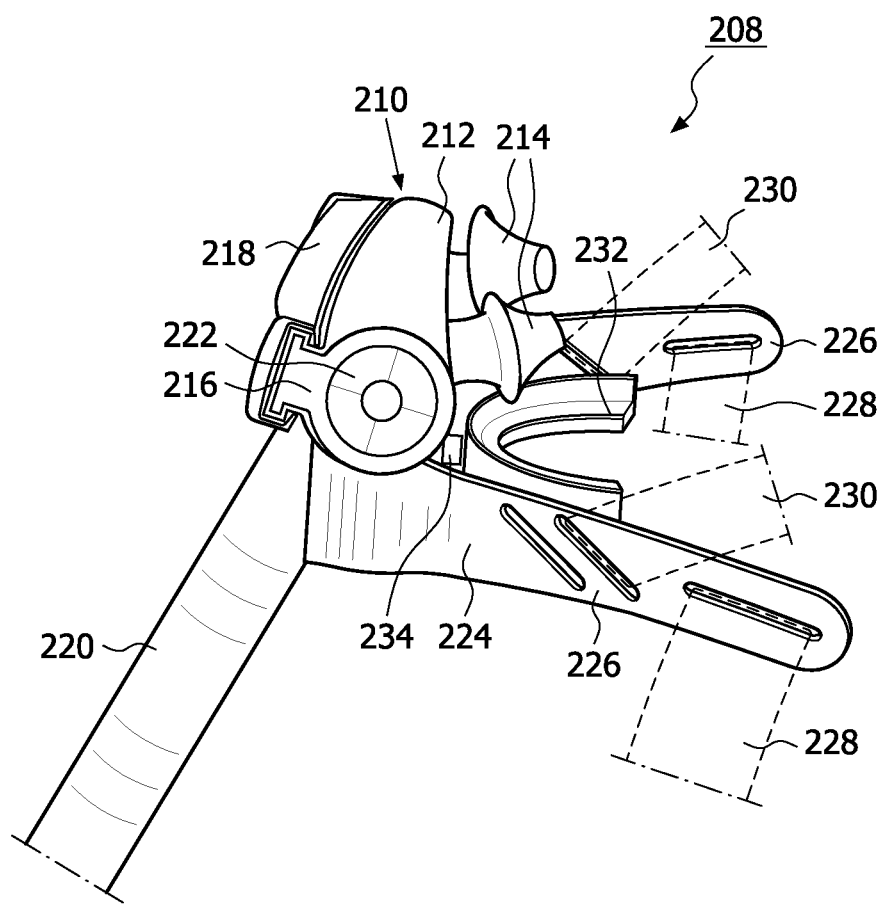
FIG. 35 is an isometric view of a patient interface device according to yet a further alternative embodiment of the invention.

FIG. 35 is an isometric view of a patient interface device 208 according to a further alternative embodiment of the present invention. The patient interface device 208 includes a nasal pillow assembly 210 that is similar to the nasal pillow assembly 6 shown in FIGS. 1 and 2. The nasal pillow assembly 210 includes a pillow sleeve 212 having nasal prongs 214. The nasal pillow assembly 210 also includes a frame 216 and a clip 218 that are similar to the frame 12 and clip 24 shown in FIGS. 1 and 2. A tube assembly 220 is attached to one side of the nasal pillow assembly 210, and an end cap 222 is attached to the opposite side of the nasal pillow assembly 210. The nasal pillow assembly 210 is supported by a chin support assembly 224 that includes arms 226, chin support strap 228 and headgear strap 230. The patient interface device 208 further includes an oral member 232, which in the particular embodiment shown in FIG. 35 comprises a bite block inserted within the patient's mouth and held between the patient's teeth. The oral member 232 is attached to the chin support assembly 224 through a connecting member 234 which may be rigid or flexible. The oral member 232 provides additional stability to the patient interface device 208 when worn by the patient. The connecting member 224 may, in one embodiment, comprise a gas flow passage that is in fluid communication with the nasal pillow assembly 6 in order to receive gas therefrom. In such an embodiment, the oral member 232 would include an opening to allow the supplied gas to enter the patient's mouth and thereafter the patient's airway.

Figure 36:
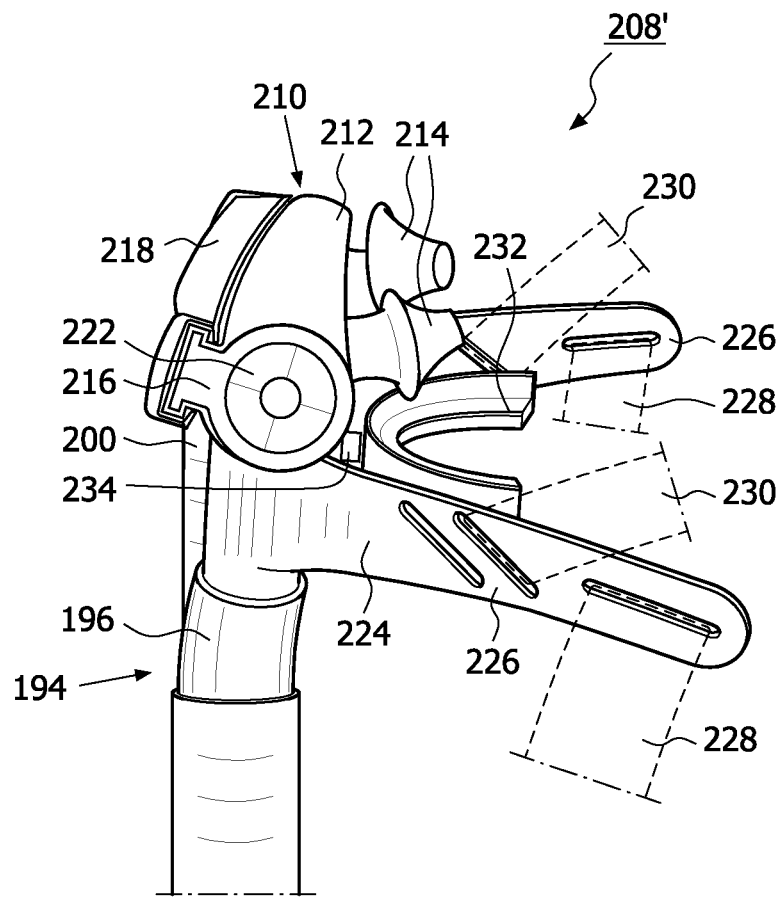
FIG. 36 is an alternative embodiment of a patient interface device that is similar to the patient interface device shown in FIG. 35.
Figure 37:
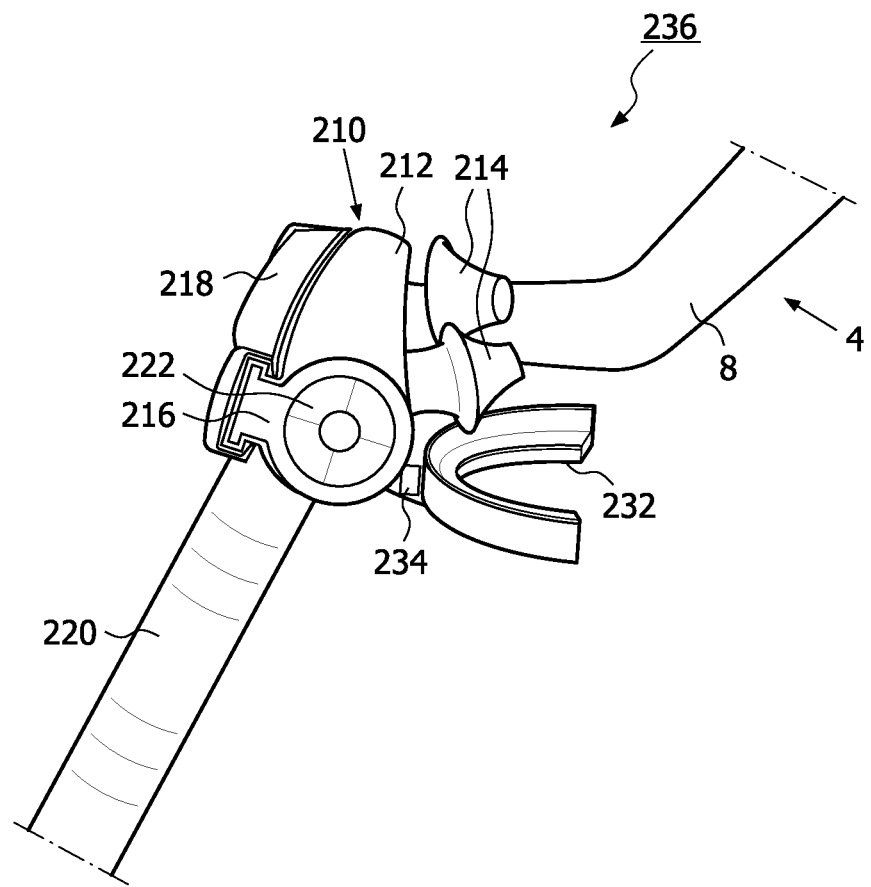
FIG. 37 is an isometric view of yet a further alternative embodiment of a patient interface device that includes an oral member.
Figure 38:
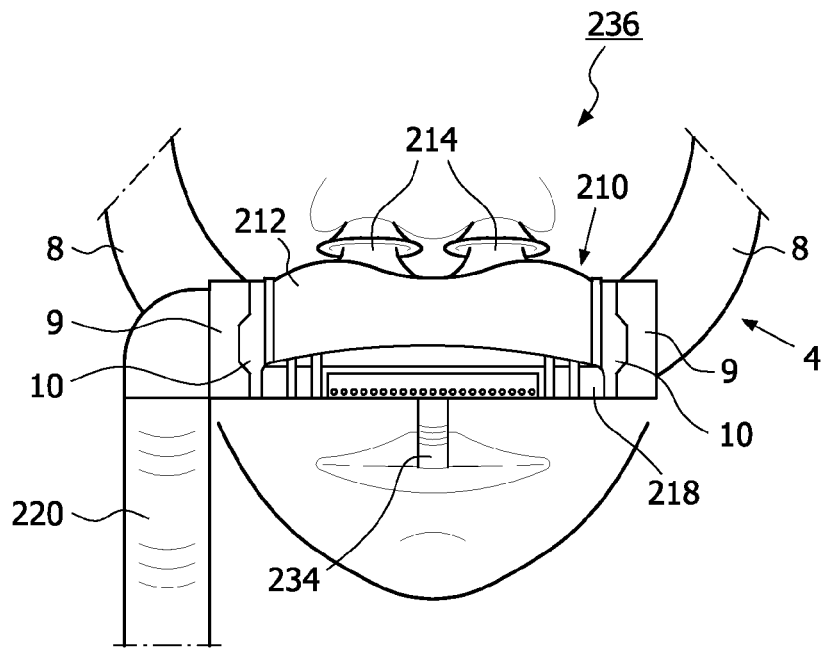
FIG. 38 is a front elevational view of the patient interface device shown in FIG. 37 being worn by a patient.

FIG. 36 is an alternate embodiment of a patient interface device 208' that is similar to the patient interface device 208 except that it includes a tube assembly 194 that is shown in FIG. 31 for the delivery of the gas to the nasal pillow assembly 210. Furthermore, although a nasal pillow assembly 210 that is similar to the nasal pillow assembly 6 is shown in FIGS. 35 and 36, it should be understood that this is meant to be exemplary only, and not limiting, and that other nasal pillow assemblies such as those shown elsewhere herein may be employed. FIG. 37 shows a further alternative embodiment of a patient interface device 236 that includes an oral member 232 as shown in FIGS. 35 and 36 but does not include the chin support mechanism 224. Instead, as shown in FIG. 37, headgear 4 having yokes 8 is provided (for ease of illustration, only one yoke 8 is shown in FIG. 37). Again, the oral member 232 provides added stability for the patient interface device 236. FIG. 38 is a front view of the patient interface device 236 shown being worn by a patient. As seen in FIG. 38, the nasal prongs 214 are received within the patient's nose and the oral member 232 is received within the patient's mouth. In addition, as shown in FIG. 38, the connecting member 234 is adapted to be bent in order to be selectively positioned for a comfortable fit.

Figure 39:
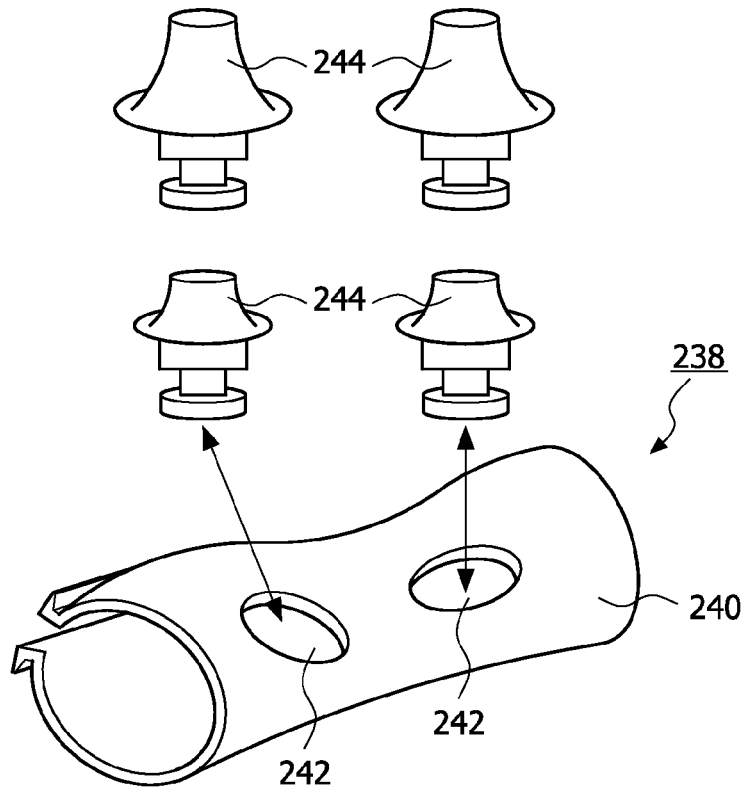
FIG. 39 is an isometric view showing a nasal pillow assembly according to still a further embodiment.

Patients which use patient interface devices such as, without limitation, the patient interface device 2 shown in FIGS. 1 and 2 often have different sized noses. As a result, different sized nasal prongs will be better suited for a particular patient depending upon the size of the patient's nose. Patient interface device 2 is often provided, therefore, with multiple pillow sleeves 14 having differing size nasal prongs 22 so that the appropriate pillow sleeve 14 can be selected by the patient. However, changing pillow sleeves 14 requires complete disassembly of the nasal pillow assembly 6, which can be time consuming and inconvenient. FIG. 39 shows a pillow sleeve assembly 238 according to another embodiment of the invention which addresses this problem. The pillow sleeve assembly 238 includes a pillow sleeve 240 having openings 242 provided therein which are adapted to receive and hold removable nasal prongs 244 of various different sizes. Thus, a patient is able to select the proper size nasal prongs 244 without the need to completely disassemble a nasal pillow assembly that includes the pillow sleeve assembly 238.

Figure 40:
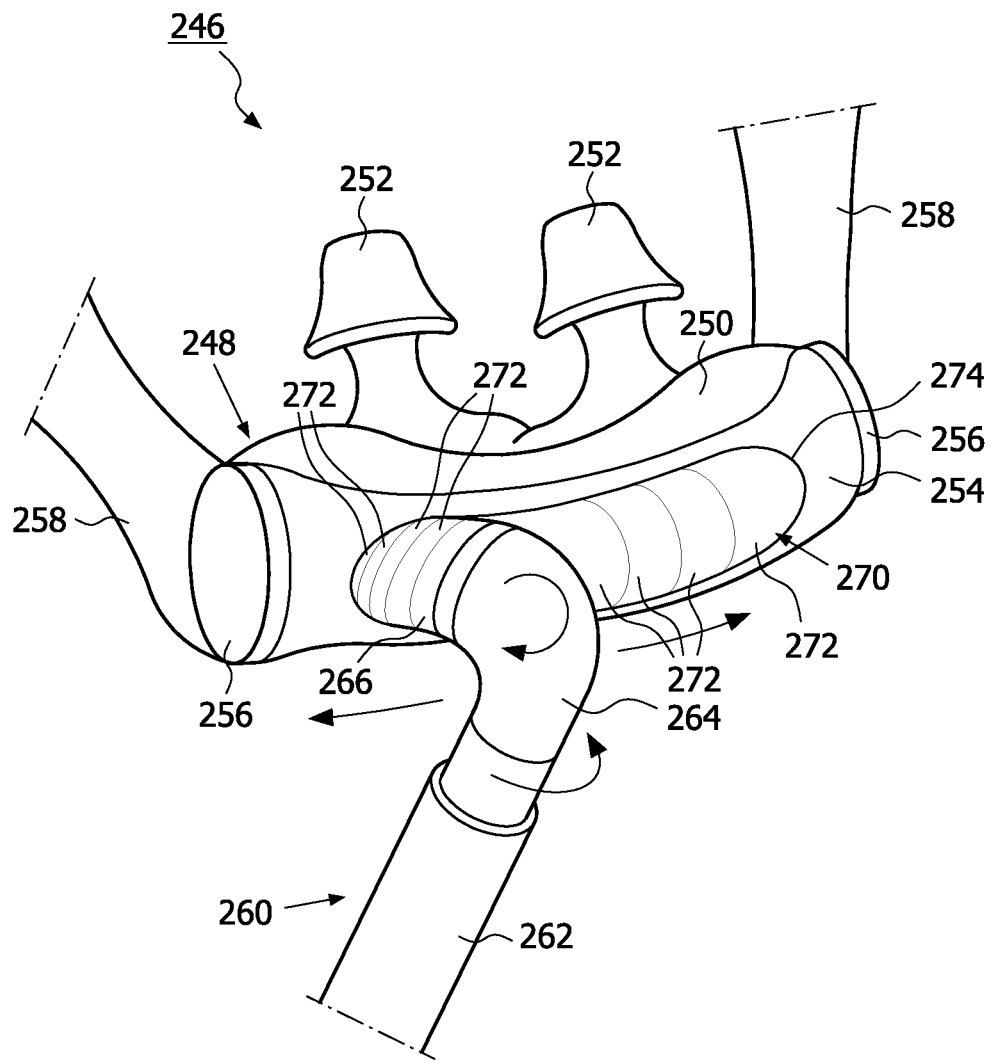
FIG. 40 is an isometric view of a patient interface device according to yet a further alternative embodiment of the invention.

FIG. 40 is an isometric view of a patient interface device 246 according to yet a further alternative embodiment of the invention. The patient interface device 246 includes a nasal pillow assembly 248 that includes a cushion portion 250 made of a flexible material such as, without limitation, silicone, having nasal prongs 252 extending therefrom. Cushion portion 250 is attached to rigid frame portion 254 by, for example, over molding the two pieces together, adhering the two pieces together using a suitable adhesive, or attaching the two pieces together using any suitable mechanical attachment mechanism. Support frame portion 254 is made of a suitable rigid material, such as, without limitation, plastic. Support frame portion 254 includes connector portions 256 structured to be attached to straps 258 of a headgear forming a part of the patient interface device 246. Furthermore, the patient interface device 246 includes a tube assembly 260 that is connected to a source of pressurized gas. The tube assembly 260 includes a main conduit 262, an elbow portion 264 and a connecting portion 266. As shown by the arrows in FIG. 40, the main conduit 262 is structured to be able to rotate relative to the elbow portion 264, the elbow portion 264 is structured to be able to independently rotate relative to the connecting portion 266, and the tube assembly 260 in its entirety is structured to be slideable along the support frame portion 254 in order to selectively position the tube assembly 260 relative to the front of the nasal pillow assembly 248.

Figure 41:
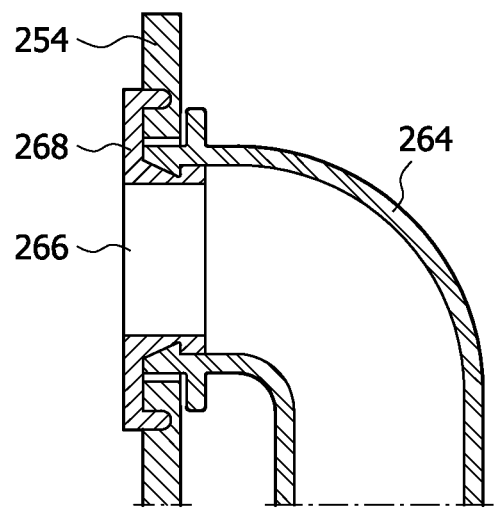
FIGS. 41 and 42 shown one embodiment for implementing the sliding tube assembly forming part of the patient interface device shown in FIG. 40.
Figure 42:
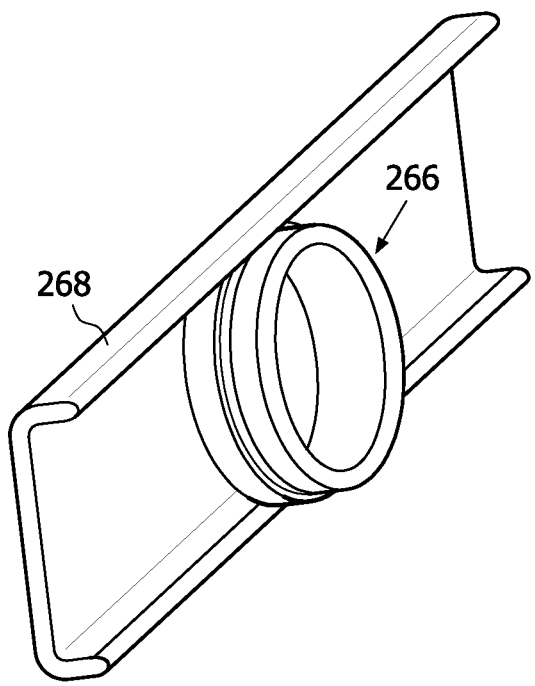

FIGS. 41 and 42 show one embodiment for implementing the sliding tube assembly 260 shown in FIG. 40. In particular, a sliding mount 268 is provided within the nasal pillow assembly 248 in sliding engagement with the support frame 254. In addition, the sliding mount engages the support frame portion 254 in a manner which maintains an airtight seal. The sliding mount includes the connecting portion 266 in the form of a snap-on connector mount which is adapted to have snap fit thereon the elbow portion 264 in a manner which provides an airtight seal. In addition, a slideable sealing mechanism having a plurality of interconnected slide elements 272 is provided within an aperture 274 provided in the support frame 254 which enables the tube assembly 260 to be slid along the aperture 274 while at the same time maintaining an airtight seal and connection between the tube assembly 260 and the nasal pillow assembly 248. The patient interface device 246, by providing for multiple degrees of selective movement of the tube assembly 260, including the ability to slide and selectively position the tube assembly along the front face of the nasal pillow assembly 248, provides for added comfort and convenience for the patient.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

What is claimed is:

1. A patient interface device, comprising:
a frame for supporting a flexible interface member, said flexible interface member being structured to deliver a gas to an airway of a patient, said frame having a flange; and
a clip including a second surface and being structured to be coupled to said frame by sliding said clip onto said flange, wherein said first surface and said second surface abut with each other when said frame and said clip are coupled, wherein said flange includes a post extending upwardly from an end portion of said first surface, wherein said clip includes a first end portion having a notch structured to receive said post firmed therein, and a second end portion opposite of the first end portion, the second end portion not having a notch structured to receive said post formed therein, wherein said post is structured to be received within said notch when said clip is slid onto said flange to permit said clip to be fully slid onto said flange when said clip is oriented such that the first end portion of the clip having the notch. corresponds with the end portion of the flange including the post, and wherein said post is structured to abut against the second end portion of the clip to prevent said clip from being fully slid onto said flange when said clip is oriented such that the second end portion of the clip not having the notch corresponds with the end portion of the flange including the post.

2. The patient interface device according to claim 1, wherein said flexible interface member comprises a pillow sleeve having a plurality of nasal prongs.

\* \* \* \* \*